(12) United States Patent
Yu et al.

(10) Patent No.: US 12,013,722 B2
(45) Date of Patent: Jun. 18, 2024

(54) COMPUTING DEVICE WITH EXTERNAL SHELL MICROPERFORATIONS

(71) Applicant: Lenovo (Singapore) Pte. Ltd., Singapore (SG)

(72) Inventors: Jonathan Jen-Wei Yu, Raleigh, NC (US); Joseph David Plunkett, Raleigh, NC (US); Jeremy Carlson, Raleigh, NC (US); Dhruvi Suresh Fulfagar, Raleigh, NC (US)

(73) Assignee: Lenovo (Singapore) Pte. Ltd., Singapore (SG)

(*) Notice: Subject to any disclaimer, the term of this patent is extended or adjusted under 35 U.S.C. 154(b) by 98 days.

(21) Appl. No.: 17/210,828

(22) Filed: Mar. 24, 2021

(65) Prior Publication Data

US 2022/0308623 A1  Sep. 29, 2022

(51) Int. Cl.
*G06F 1/16* (2006.01)
*A61L 2/10* (2006.01)
*A61L 2/26* (2006.01)

(52) U.S. Cl.
CPC .............. *G06F 1/1616* (2013.01); *A61L 2/10* (2013.01); *A61L 2/26* (2013.01); *G06F 1/1656* (2013.01); *G06F 1/1688* (2013.01); *A61L 2202/11* (2013.01); *G06F 1/1647* (2013.01)

(58) Field of Classification Search
CPC ........... G06F 1/1613–26; G06F 1/1616; G06F 1/1656; A61L 2/10; A61L 2/26; A61L 2202/11

See application file for complete search history.

(56) References Cited

U.S. PATENT DOCUMENTS

| | | | |
|---|---|---|---|
| 11,275,482 B2* | 3/2022 | Osterhout | G06F 3/017 |
| 11,341,765 B2* | 5/2022 | Rhee | G01L 1/162 |
| 11,353,933 B2* | 6/2022 | Xu | G06F 1/1681 |
| 11,455,015 B2* | 9/2022 | Stewart | G06F 1/1694 |
| 2019/0235608 A1* | 8/2019 | Shin | A45C 11/00 |
| 2021/0373610 A1* | 12/2021 | Xu | G06F 1/1681 |

* cited by examiner

*Primary Examiner* — James Wu
(74) *Attorney, Agent, or Firm* — Brian J. Pangrle

(57) ABSTRACT

A computing device can include a processor; memory accessible to the processor; a display operatively coupled to the processor; and an external shell assembly that includes an array of electronic components, where the array of electronic components includes transducers.

20 Claims, 15 Drawing Sheets

COMPUTING DEVICE WITH EXTERNAL SHELL MICROPERFORATIONS

TECHNICAL FIELD

Subject matter disclosed herein generally relates to technology for computing devices and display devices.

BACKGROUND

Various types of devices, display devices, computing and display devices, etc., exist that include various components.

SUMMARY

A computing device can include a processor; memory accessible to the processor; a display operatively coupled to the processor; and an external shell assembly that includes an array of electronic components, where the array of electronic components includes transducers. Various other apparatuses, systems, methods, etc., are also disclosed.

BRIEF DESCRIPTION OF THE DRAWINGS

Features and advantages of the described implementations can be more readily understood by reference to the following description taken in conjunction with examples of the accompanying drawings.

DETAILED DESCRIPTION

The following description includes the best mode presently contemplated for practicing the described implementations. This description is not to be taken in a limiting sense, but rather is made merely for the purpose of describing general principles of various implementations. The scope of invention should be ascertained with reference to issued claims.

Figure 1:
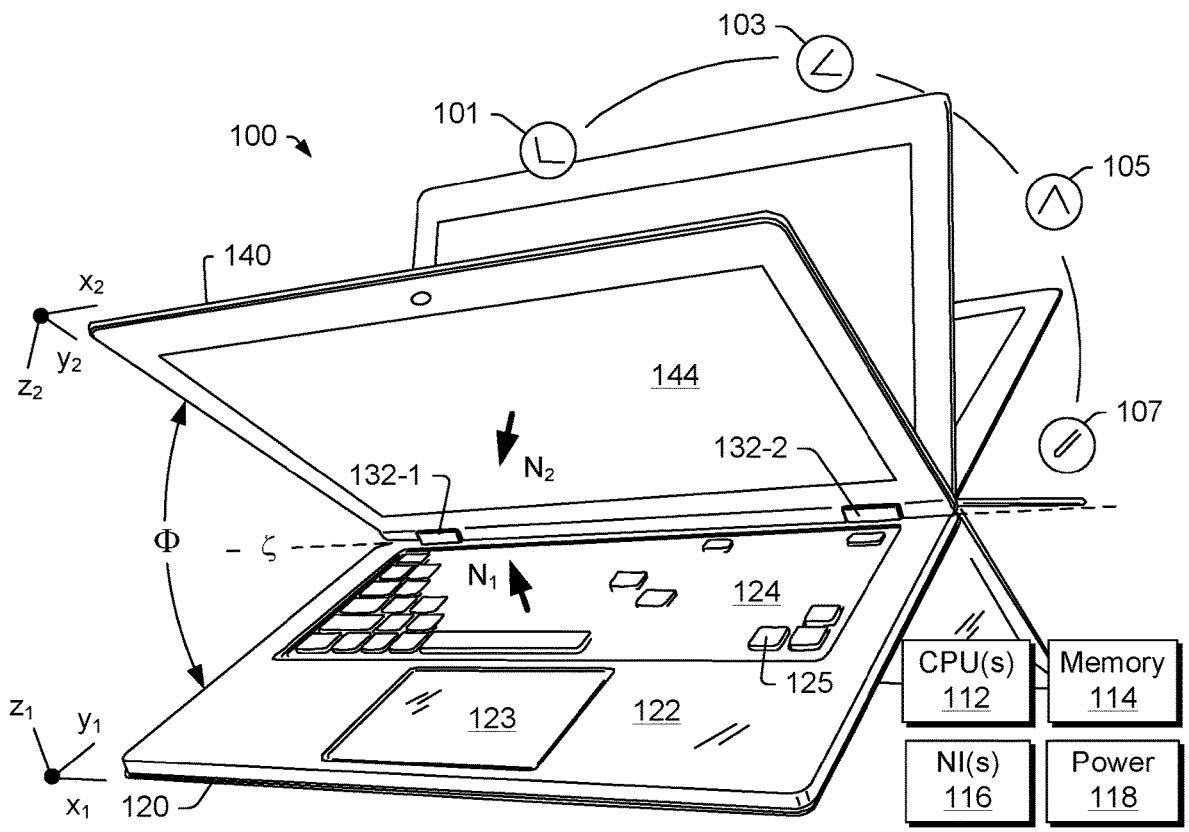
FIG. 1 is a diagram of an example of a device.
Figure 1:
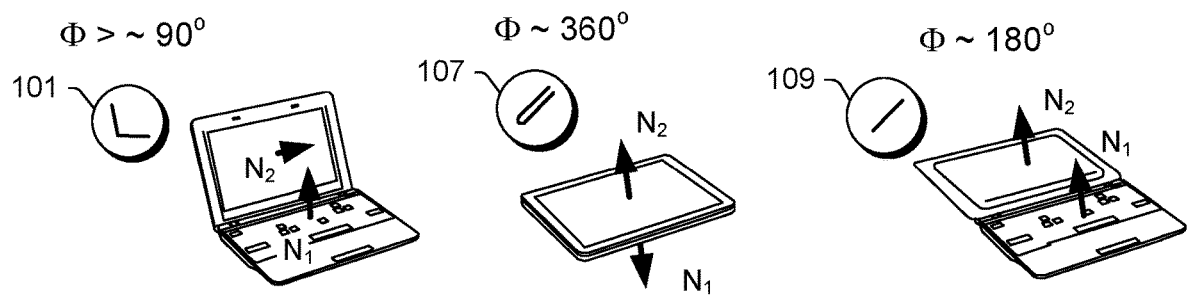

FIG. 1 shows an example of a computing device 100 that includes a keyboard housing 120 and a display housing 140 that are pivotable with respect to each other via movement about one or more hinges 132-1 and 132-2 (e.g., hinge assemblies). The computing device 100 may be a system such as, for example, a computing system (e.g., an information handling device, etc.).

As an example, the computing device 100 may include one or more processors 112, memory 114 (e.g., one or more memory devices), one or more network interfaces 116, and one or more power cells 118. Such components may be, for example, housed within the keyboard housing 120, the display housing 140, or the keyboard housing 120 and the display housing 140.

As shown in the example of FIG. 1, the keyboard housing 120 includes a keyboard 124 with keys 125 and the display housing 140 includes a display 144. In such an example, the keyboard 124 is defined in a first Cartesian coordinate system as having a width along an x-axis ($x_1$), a depth along a y-axis ($y_1$) and a height or thickness along a z-axis ($z_1$) that extends in a direction outwardly away from touch surfaces of keys 125 of the keyboard 124 and the display 144 is defined in a second Cartesian coordinate system as having a width along an x-axis ($x_2$), a depth along a y-axis ($y_2$) and a height or thickness along a z-axis ($z_2$) that extends in a direction outwardly away from a viewing surface of the display 144. As an example, a coordinate system may be right-handed or left-handed.

As shown in the example of FIG. 1, the one or more hinges 132-1 and 132-2 pivotably connect the keyboard housing 120 and the display housing 140 for orienting the display housing 140 with respect to the keyboard housing 120. For example, orientations may include orientations definable with respect to an axis (e.g., or axes) such as the axis ζ and an angle Φ about that axis.

FIG. 1 shows some examples of orientations 101, 103, 105, 107 and 109. The orientations 101, 103, 105, 107 and 109 may correspond to orientations of a clamshell computing system. The orientation 101 may be a notebook orientation where the angle Φ is about 90 degrees or more (e.g., or optionally somewhat less than about 90 degrees depending on position of a user, etc.). As shown, for the orientation 101, a user may use a finger or fingers of one or both hands to depress keys 125 of the keyboard 124 (e.g., touch typing), for example, while viewing information being rendered to the display 144 of the display housing 140 (e.g., using the one or more processors 112, the memory 114, etc. that may be included in the keyboard housing 120, the display housing 140 or both).

As an example, the keyboard housing 120 may include a frontal surface 122 and may include a touch input surface 123 (e.g., of a touch input device such as a touchpad). As an example, the keyboard 124 may include one or more other input devices (e.g., a control stick, etc.). As an example, the frontal surface 122 may be a surface suitable for resting a palm or palms of a hand or hands. For example, as shown in FIG. 1, the touch input surface 123 can be defined by x and y dimensions where a left palm rest surface is to the left of the touch input surface 123 and where a right palm rest surface is to the right of the touch input surface 123. In such an example, the left and right palm rest surfaces may be defined by respective x and y dimensions as well as a spacing therebetween. Where a system does not include a touch input surface such as the touch input surface 123, the frontal surface 122 may extend in the y direction approximately from a left side of the keyboard housing 120 to a right side of the keyboard housing. Such a surface can be a left and right palm rest surface.

A palm rest surface can allow a user to rest a palm or palms while the user may type (e.g., touch type) using keys of a keyboard that is part of a keyboard housing. For example, a user can rest a palm on a palm rest surface while using one or more finger tips (e.g., or finger pads) to touch keys to thereby instruct a computing device to receive input instructions. In such an example, the keys of the keyboard may be depressible keys. A depressible key may include a spring mechanism that allows the key to be, responsive to finger applied force, depressed a distance in the z direction of the Cartesian coordinate system of a keyboard housing to a level that may be a maximum depression level where, upon release of the force, the key may then return to an undepressed level.

As to the orientation 103, it may correspond to a display orientation for viewing the display 144 where the keyboard 124 faces downward and the computing device 100 is supported by the keyboard housing 120 (e.g., by a rim about the keyboard 124, the frontal surface 122, etc.). As to the orientation 105, it may correspond to a "tent" orientation where the display 144 faces outwardly for viewing on one side of the tent and the keyboard 124 of the keyboard housing 120 faces outwardly on the other side of the tent.

The orientation 107 may be a tablet orientation where the angle Φ is about 360 degrees such that a normal outward vector $N_1$ of the keyboard 124 of the keyboard housing 120 and a normal outward vector $N_2$ of the display 144 of the display housing 140 are oriented in oppositely pointing directions, pointing away from each other; whereas, in contrast, for a closed orientation of the computing device 100 (e.g., where the angle Φ is about 0 degrees), the vectors $N_1$ and $N_2$ would be pointing toward each other.

In the orientation 107, the keyboard 124 has its keys 125 pointing outwardly in the direction of the vector $N_1$. Where the keys 125 are depressible keys, when a user grasps the computing device 100, the keys 125 may be contacted by the users hand or hands. A user may perceive the springiness of the keys 125 as being somewhat undesirable. For example, springy keys may interfere with a user's ability to comprehend or sense force that is sufficient to grasp the computing device 100, which may cause the user to grasp too lightly or to grasp too strongly, which may possibly impact integrity of the keys (e.g., springs, spring-mechanisms, contacts, etc.). Further, if the user repositions her hand or hands, the user may experience the springiness again. In contrast, a surface without such depressible keys may have a more even feel to a user and may be less distracting. An arrangement that allows for such a surface may include a single hinge that allows for pivoting a keyboard housing with respect to a display housing such that keys of the keyboard housing can be oriented to face a back side of a display housing (a side opposite the display). In such an approach, a user may spin the keyboard housing by 180 degrees about a central axis of the single hinge (e.g., an axis orthogonal to the axis ζ and then rotate the keyboard housing such that the keys face the back side of the display in a folded orientation. In such an example, a single centrally located hinge provides symmetry such that a computing system can be aligned in a clamshell closed orientation and a tablet orientation, optionally with the keys of the keyboard housing facing the back side of a display of a display housing.

The orientation 109 may be a planar orientation where the angle Φ is about 180 degrees such that a normal outward vector $N_1$ of the keyboard 124 of the keyboard housing 120 and a normal outward vector $N_2$ of the display 144 of the display housing 140 are oriented in approximately the same pointing directions.

Various computing systems such as laptop or notebook computing devices can be characterized at least in part by a footprint. For example, the computing device 100 of FIG. 1 may be characterized at least in part by dimensions in x and y as to the keyboard housing 120 and/or as to the display housing 140. As an example, a footprint can be an area that can be defined by a plane in the x and y directions of the Cartesian coordinate systems shown in FIG. 1.

Figure 2:
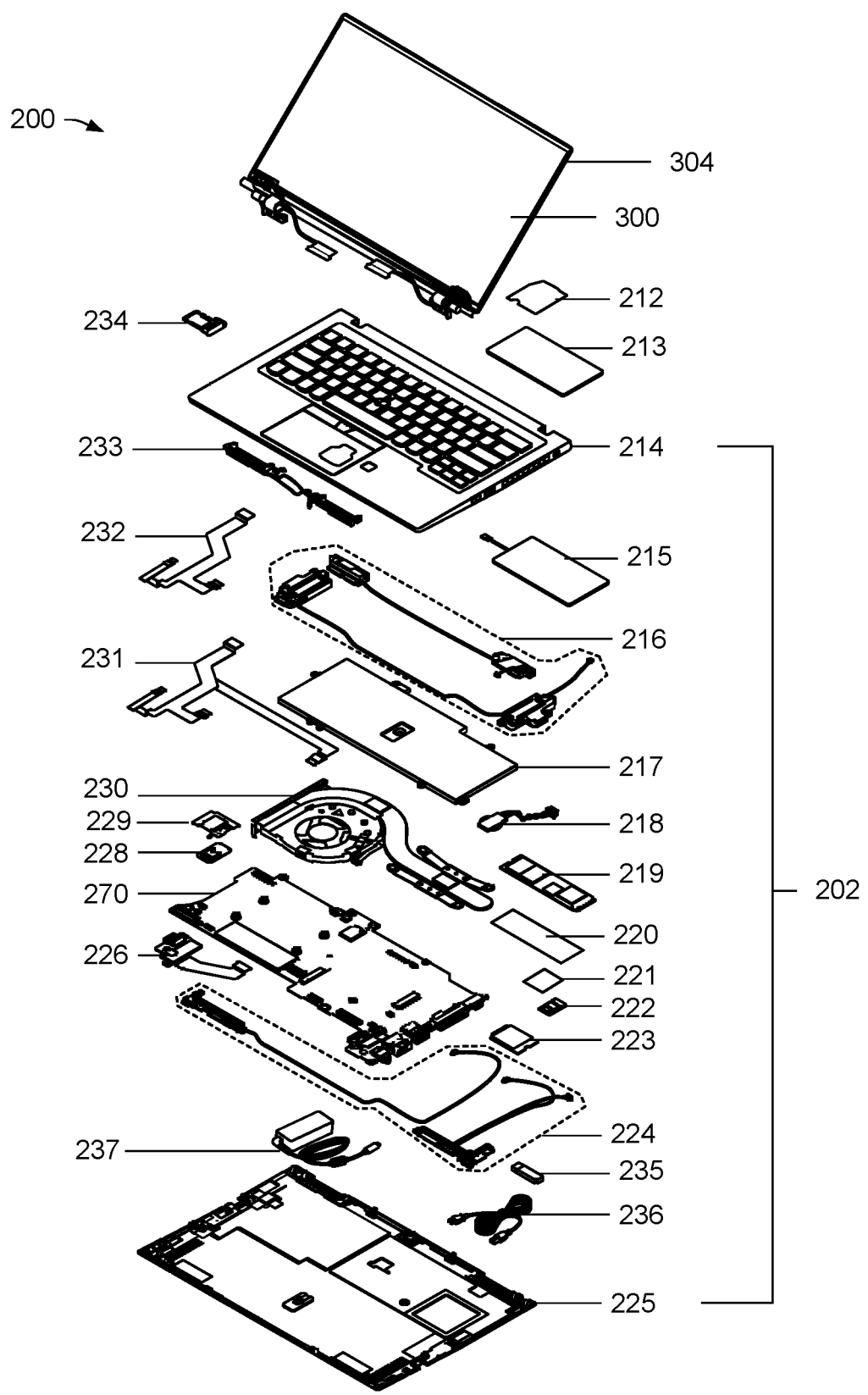
FIG. 2 is a diagram of an example of a device.

FIG. 2 shows an exploded perspective view of a computing device 200 as including various components, which can include, for example, a display assembly 300, insulation trackpad tape 212, a trackpad 213 or 215, a keyboard bezel assembly with keyboard 214, a speaker kit 216, a built-in battery 217, a coin-cell battery 218, a solid-state drive 219, a thermal pad 220, NFC module foam 221, a NFC module 222, a wireless-WAN card 223, a wireless-WAN antenna assembly 224, a base cover assembly 225, a USB and power board 226, a system board 270, a fingerprint reader module 228, a fingerprint reader bracket 229, a thermal fan assembly 230, a trackpad and fingerprint reader cable 231 or 232, a wireless-LAN antenna assembly 233, a SIM-card tray 234, a recovery USB 235, a power cord 236, and an AC power adapter 237. As an example, the computing device 100 of FIG. 1 can include one or more of the features of the computing device 200 of FIG. 2.

As shown in the example of FIG. 2, the display assembly 300 can include a display housing 304 and the computing system 200 can include a keyboard housing 202, for example, formed at least in part via the keyboard bezel assembly with keyboard 214 and the base cover assembly 225.

Figure 3:
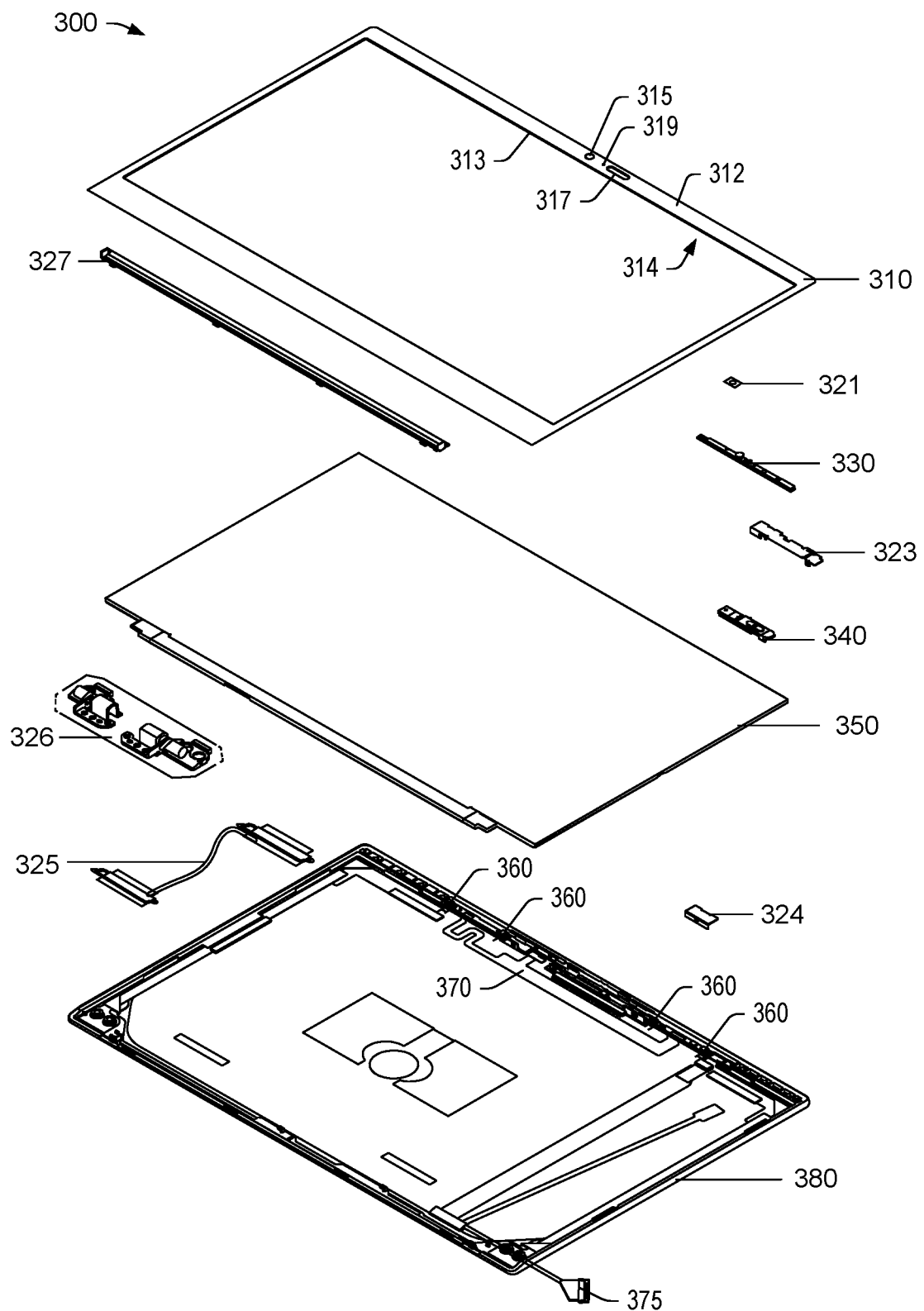
FIG. 3 is a diagram of an example of a display assembly of the device of FIG. 2.

FIG. 3 shows an exploded perspective view of the display assembly 300 of FIG. 2 as including various components, which can include, for example, a bezel 310, a foam component for an IR LED camera 321, a camera module 330, a stopper 323, a shutter 340, a display panel 350, a support plate 324, one or more microphones 360, wiring 370, one or more wiring connectors 375, a back side (rear) cover assembly 380, a display cable 325, one or more hinge assemblies 326, and a display bezel frame component 327.

In the example of FIG. 2 and FIG. 3, the computing device 200 can include various media capture components. For example, a camera can be a media capture component, a microphone can be a media capture component, etc. A media capture component may be an audio media capture component, a video media capture component, a still image media capture component, etc.

As shown, the bezel 310 includes a front surface 312 and an opposing rear surface 314 where various openings extend between the front surface 312 and the rear surface 314. For example, as shown, the bezel 310 includes a display opening 313, a camera opening 315, a shutter control opening 317, and an IR camera opening (e.g., where an IR camera is included, noting that a camera may be a combined visible and IR camera).

As shown, the camera module 330 couples to the back side cover assembly 380 where the wiring 370 operatively couples to the camera module 330 and to the one or more microphones 360. The display assembly 300 can be operatively coupled to other circuitry of the computing device 200, for example, via the one or more wiring connectors 375.

In the example of FIG. 2 and FIG. 3, the display housing 304 can couple to the keyboard housing 202 via one or more hinge assemblies such as, for example, one or more of the hinge assemblies 326.

Figure 4:
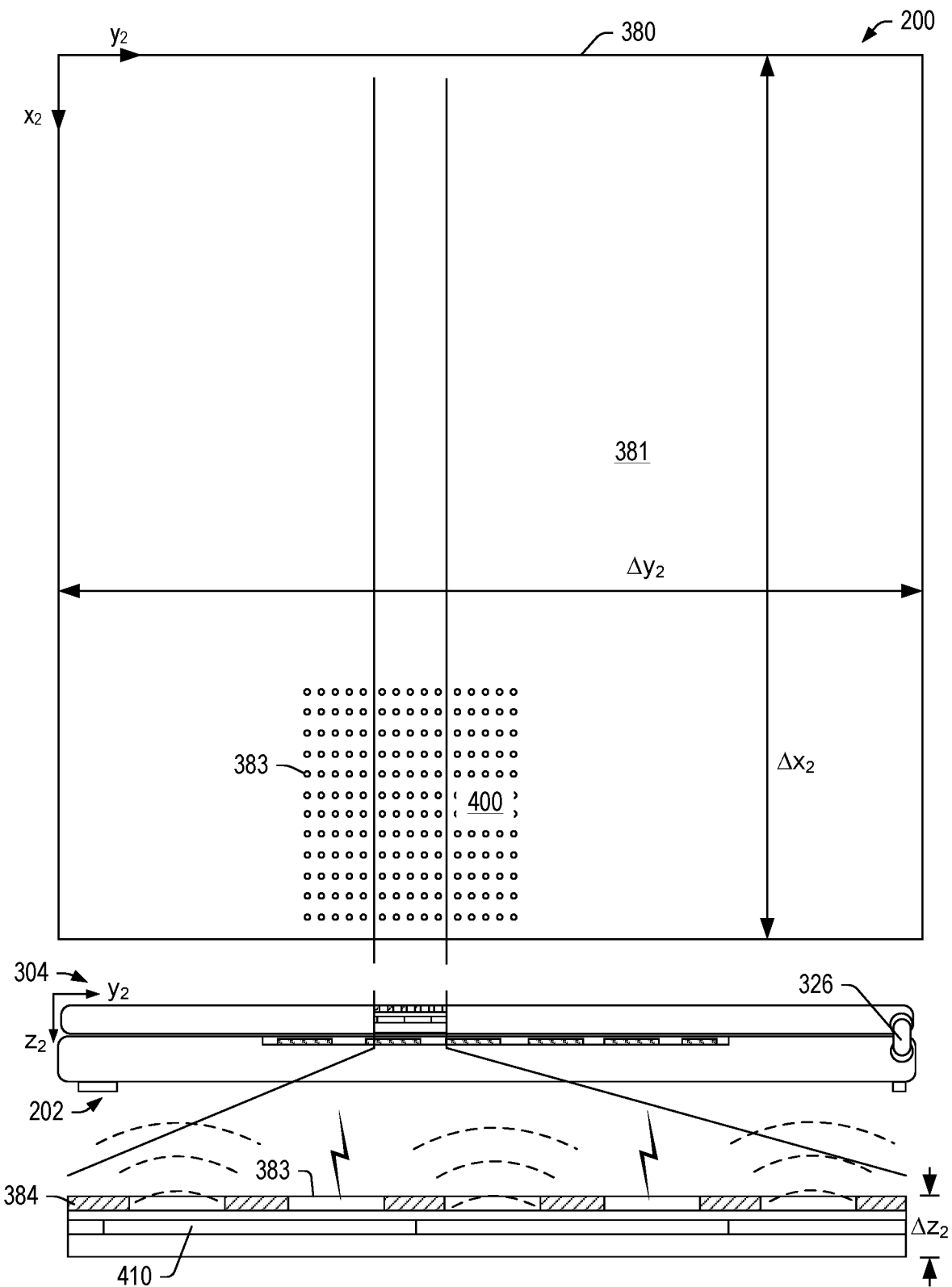
FIG. 4 is a diagram of an example of a device that includes an array.

FIG. 4 shows an example of the computing device 200 as including an array of electronic components 400. Various features may be described with reference to a coordinate system or coordinate systems. For example, a Cartesian coordinate system is shown in FIG. 4 ($x_2$, $y_2$ and $z_2$) where dimension of the display housing 304 can include $\Delta x_2$, $\Delta y_2$, and $\Delta z_2$. As an example, the thickness $\Delta z_2$ of the display housing 304 may be less than approximately 20 mm. As an example, an electronic component may be of a thickness less than approximately 15 mm and, as to a display housing, may be positioned within a footprint of a display panel, in a bezel region about a display panel, etc.

As an example, a MEMS electronic component may be of a thickness less than approximately 10 mm, for example, consider a MEMS speaker array with an array of individual MEMS speakers where the MEMS speaker array may be of a thickness less than approximately 10 mm. As an example, a MEMS speaker (e.g., as an individual electronic component) may be of a thickness less than approximately 5 mm, etc., where such an array may be formed of such individual MEMS speakers, etc. As explained, an electronic component can be a transducer and, for example, may be of a thickness that is less than 5 mm. Above, speakers are given as an example of a type of transducer where an array may include one or more types of transducers.

In the example of FIG. 4, the cover assembly 380 includes a surface 381 with openings 383. For example, the cover assembly 380 can include a shell 384 that includes the openings 383 where the array of electronic components 400 can be in fluid communication with an air space or air spaces beneath the shell 384 and an ambient air space exterior to the shell 384 (e.g., in contact with the surface 381). As an example, the cover assembly 380 can be a shell assembly that includes a shell such as the shell 384.

As shown in the example of FIG. 4, the array of electronic components 400 can include individual electronic components such as an electronic component 410, which may be a unit with one or more types of circuitry. For example, a unit can include a piezo circuit, a light emitting circuit, a membrane coupled circuit, etc. In such an example, the openings 383 can provide for one or more of material properties of the shell 384, passage of air through the shell 384, passage of light through the shell 384, passage of other radiation through the shell 384, etc.

As to material properties of the shell 384, the openings 383 may increase the resiliency of the shell 384. For example, the modulus of resilience of the material of the shell 384 may be controlled through size, shape, number and/or spacing (e.g., density) of the openings 383. Resilience pertains to the capability of a material (e.g., an object) to consume energy where, within its elastic limit, it will withstand the energy and, upon release of the energy, return back to its original shape (e.g., elastic deformation rather than plastic deformation). The modulus of resilience can be defined as an amount of energy that a material can absorb and still return to its original position (e.g., shape). In such an approach, the area under the elastic portion of the stress-strain curve for that material and the modulus of resilience as µ or $U_r$ for a given compound can be given as: $U_r = \sigma^2/(2E)$. In the foregoing equation, $U_r$ (e.g., or µ) is the modulus of resilience, σ is the yield strain and E is Young's modulus.

As to force that may be applied to the surface 381, consider a force that may be akin to that of a finger force applied during touch-typing on a keyboard with depressible keys. For example, consider a force that may be less than approximately 10 N, less than approximately 6 N or less than approximately 4 N. As an example, a key switch make force for a keyboard key may be less than approximately 1 N. In the example of FIG. 4, where the shell 384 is resilient, it may deform elastically in response to a force greater than approximately 0.25 N where, for example, deformation may be local such that one or more electronic components in a deformed region can be actuated, generate a signal, etc. As an example, the shell 384 may be configured for allowing electronic component actuating, signal generation, etc., without deformation. For example, consider an approach where one of the openings 383 in the shell 384 can provide for fluid pressure (e.g., air pressure) sensing, etc. As an example, the shell 384 may be elastically deformable while also providing for fluid pressure based sensing via one or more of the openings 383.

As an example, the shell 384 may be coupled to one or more piezo components and/or disposed above one or more piezo components. In such an example, where the shell 384 is resilient, deformation of the shell 384 may cause strain of one or more piezo components, which can generate a signal or signals in response. As an example, where an electronic component includes a membrane, resiliency of the shell 384 may provide for deformation of the membrane, which, in turn, may generate and/or alter a signal. As an example, a piezo component can include a membrane where deformation of the membrane causes the piezo component to generate a signal, alter a signal, etc.

As to passage of air, an opening may allow for passage of air into a region within a housing and/or allow for passage of air out of a region within a housing. For example, consider a speaker that includes a membrane and a driver that is coupled to the membrane. In such an example, an electrical signal applied to the driver can cause the membrane to move and generate longitudinal waves. As to a reverse action, consider placing a finger over an opening or openings where depending on how the finger is placed air pressure may increase in a manner that is sufficient to cause a membrane to move where, if the membrane is coupled to circuitry, the movement may generate a signal.

As an example, an electronic component that includes a membrane may provide for sensing responsive to movement of the membrane where the membrane may be actuated. For example, where a membrane is driven within a chamber, force to move the membrane may depend on whether the chamber includes an opening or not. In a closed chamber, the force may be increased (e.g., increased resistance to movement of the membrane), which may be measurable (e.g., via an amount of power, etc.). As an example, where a finger is positioned over an opening such that the opening is closed, a membrane-based electronic component may be able to detect the presence of the finger closing the opening through a drive signal that aims to move the membrane. As an example, an array can include one or more electronic components that may operate in a sensing state where, when an opening or openings are closed, the array can detect such closure or closures. For example, consider a low level vibration state where membrane movement may cause air movement (e.g., waves) through openings where the air movement is below an audible range (e.g., in intensity and/or frequency) to a human (e.g., consider below 20 Hz and/or above 20 kHz in frequency).

As to passage of light, consider a light emitting diode (LED) that can emit light where at least a portion of the emitted light can directly and/or indirectly pass from an interior side to an exterior side of a shell through an opening or openings. Visible light may be considered to be a type of radiation, for example, electromagnetic radiation as can be defined using an electromagnetic spectrum.

As to another type of radiation, consider a type of ultraviolet radiation, which may be UVA, UVB and/or UVC.

In such an example, illumination of a UV LED may provide for sterilization of a shell. For example, consider a user that desires sterilization of the surface 381 where the array 400 includes one or more UV LEDs, etc.

As an example, a computing device can include one or more of a far UVC/deep-ultraviolet LED or another type of solid-state device (e.g., an excimer source, etc.). As an example, an emitter may include one or more filters, which may act to filter wavelengths that may be damaging to a human and/or a filter may be used to limit longer wavelengths.

As an example, a computing device can include one or more nitride semiconductor chips that can be solid-state electronic components that can emit far-UVC light at wavelengths ranging from approximately 200 nanometers to approximately 222 nanometers.

An article by Hirayama et al., entitled "222 nm Deep-Ultraviolet AlGaN Quantum Well Light-Emitting Diode with Vertical Emission Properties" (March 2010, Applied Physics Express 3(3), DOI: 10.1143/APEX.3.032102) is incorporated by reference herein and describes a 222 nm deep-ultraviolet (DUV) AlGaN multi-quantum well (MQW) light-emitting diode (LED) fabricated on a high-quality AlN buffer layer grown on a sapphire substrate where a maximum output power and external quantum efficiency of the 222 nm AlGaN LED were 14 muW and 0.003 percent, respectively, under pulsed current injection.

As an example, far-UVC radiation may be utilized for sterilization, deactivating biological entities, etc. Certain wavelengths of UVC such as far-UVC may pose less risk to humans while still being capable of crippling target viruses and/or other biological materials (e.g., whether live or not).

As an example, a computing device may include one or more fans where one or more radiation emitting electronic components can emit radiation into an air stream driven at least in part by the one or more fans. As an example, a computing device may include microperforations in a shell that can provide for transmission of air into and/or out of the computing device where such air may be exposed to radiation emitted by one or more electronic components.

As an example, an electronic component may be a sensor such as, for example, a light to energy sensors (e.g., a light detector, etc.). In such an example, light may pass through one or more openings to the sensor. For example, consider a sterilization mode of operation that occurs responsive to a signal from one or more sensors. In such an example, a tiered approach may be utilized. For example, consider a decrease in light being detected because one or more openings are soiled to some degree. In such an example, upon reaching a soiling limit, an array may activate one or more UV sources responsive to a low level of light being detected such as, for example, at nighttime during non-use of a device, while a device is in a case or bag, etc. In such an example, the sensor may serve multiple purposes including one or more of detecting a soiled opening and/or ambient light level. Activing a UV source or sources at a time when a user is not likely looking at openings in a shell may help to protect the user from UV radiation. As an example, a UV approach may be timed, for example, consider a pulsed approach where pulses may be relatively short yet cumulative in their effect to sterilize. As an example, a shell or other component may include a material that fluoresces upon exposure to UV radiation. For example, consider one or more minerals (e.g., fluorite, calcite, gypsum, ruby, talc, opal, agate, quartz, and amber) and/or one or more optical brighteners. As an example, a shell or other component may include a material that phosphoresces upon exposure to UV radiation. Phosphorescence is a process in which energy absorbed by a substance is released relatively slowly in the form of light. A phosphorescent material may include zinc sulfide, calcium sulfide, strontium aluminate, etc. Strontium aluminate has a luminance approximately 10 times greater than zinc sulfide where strontium aluminate based pigments have been used in products such as exit signs. Where one or more UV sources are present in an array, a photoluminescent material or materials (e.g., fluorescent, phosphorescent, etc.) may be utilized to create a visual effect. For example, consider a phosphorescent material that can glow for a period of time after exposure to UV radiation, which may indicate that a UV sterilization process has been performed.

As an example, an approach to sterilization and/or cleaning may include activating one or more speakers. In such an example, energy transmitted to air and/or to a shell may be sufficient to unblock one or more openings, release debris from one or more openings and/or the shell, etc.

As an example, an electronic component may be provided as a surface mount electronic component. For example, consider a surface mount LED that may provide for emission of one or more wavelengths, colors, etc. As an example, consider a micro LED such as a bi-color micro LED with dimensions of approximately 3.2 mm×2.8 mm×1.9 mm, which may be controlled to emit one of two colors (e.g., red/green, yellow/green, etc.). As an example, a micro LED may be of a thickness less than approximately 5 mm, less than approximately 2 mm, etc. (e.g., consider an OSRAM Micro SIDELED 3010 that has dimensions of approximately 3 mm×1 mm×1 mm).

As to transmission of radiation, one or more light pipes may be utilized, for example, consider an LED positioned with respect to one or more light pipes that may be disposed in an opening such as a microperforation as an opening. In such an example, a light pipe may transmit radiation to a sensor and/or transmit radiation from an emitter.

As an example, an electronic component can be a sensor that may detect reflected radiation. For example, consider an LED that can emit light via an opening where the presence of an object that covers the opening or that is otherwise placed above the opening can reflect a portion of the emitted light where a sensor can detect the reflected portion of the emitted light. For example, consider a light to digital sensor, a light to voltage sensor, a light to frequency sensor, etc. As an example, consider the ams TSL237T light to frequency converter sensor (e.g., transducer) that is a four-lead surface mount electronic component with dimensions of approximately 3.8 mm×2.6 mm×1.35 mm with a photoactive area of approximately 1 mm×1 mm. Such a component may be positioned beneath a microperforated shell and proximate to one or more LEDs such that one or more of ambient radiation (e.g., ambient light), presence of an object such as a finger that causes reflection of LED emitted radiation, etc., can be sensed by the light to frequency converter sensor. In such an example, output from the sensor may be utilized as a control signal, for example, to call for one or more actions, which may be for an LED and/or other circuitry. As an example, a microperforated shell may include a spacing between an inner facing surface and an electronic component where the inner facing surface may be reflective, non-reflective, etc., as to radiation (e.g., light). For example, where the surface is non-reflective to light (e.g., low reflection), a finger above an opening or openings (e.g., microperforations) may increase reflection of radiation.

In various instances, a number of electronic components may be provided on a tape, for example, on a reel. In such an example, a tape space may be utilized for positioning electronic components in an array and/or electronic components may be removed from the tape and positioned in an array at a desired spacing.

As an example, the device 200 can include the array 400 as being a multifunctional array, which may include one or more of different types of electronic components, which may be operable in one or more manners for one or more purposes (e.g., individually, in groups of two or more, etc.).

As an example, a computing device can include a shell that covers one or more types of electronic components (e.g., in an array) that are transducers (e.g., electric-light, light-electric, electric-motion, motion-electric, chemical-electric, electric-chemical, etc.).

As an example, a computing device can include an array of electronic components where the electronic components may include one or more types of batteries. As an example, consider ultra-thin batteries that may be operable independent of a main battery of a computing device and, for example, be built into an external shell assembly (e.g., batteries that may be rechargeable or non-rechargeable) for operation of electronic components of an array, optionally when a processor of the computing device is not powered. As an example, an ultra-thin battery may be a battery having a 1 mm thickness or less (e.g., less than approximately 0.6 mm). As an example, a non-rechargeable battery may be sufficient for powering one or more electronic components over an expected lifetime of a computing device, for example, where the power requirements of the one or more electronic components may be quite low.

An array of electronic components may be positioned in one or more regions of a computing device such as, for example, in and/or adjacent to an external shell. As an example, regions may include a bezel region, a palm rest region, etc. As an example, an array of electronic components may be positioned next to a unitary electronic component such as a touch-pad (e.g., a touch-pad being a unitary component rather than an array of electronic components), an LED display (e.g., an LED display being a unitary component rather than an array of electronic components), etc.

As an example, an external shell may be a composite shell where MEMS components can be embedded, optionally with ultra-thin batteries. As various MEMS components may be low power, one or more types of non-rechargeable batteries may be sufficient for years of use. As an example, one or more non-rechargeable batteries may be utilized responsive to one or more conditions such as, for example, when a main battery of a computing device is discharged, when a computing device closed, when a processor is powered off, etc.).

Figure 5:
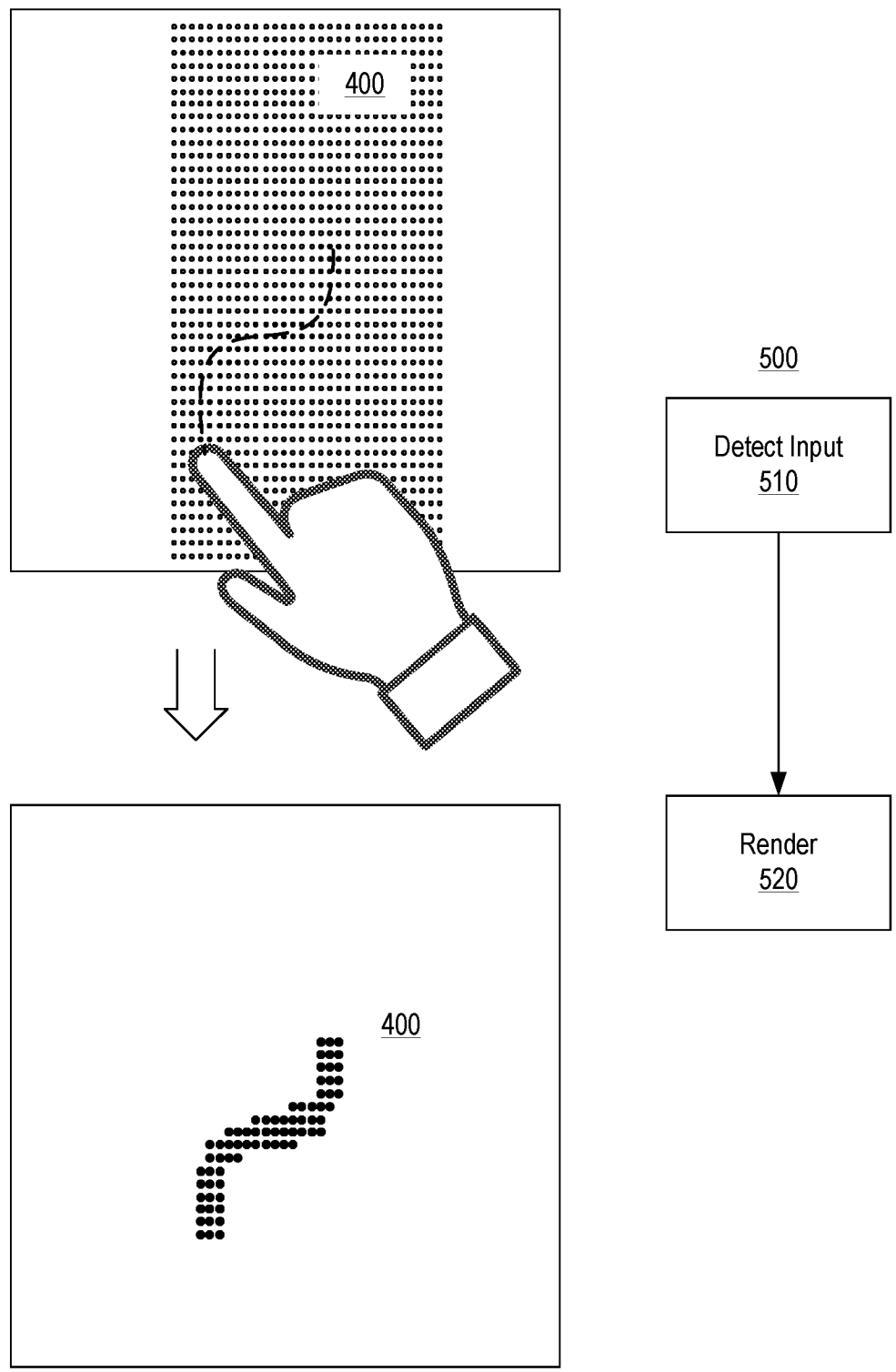
FIG. 5 is a series of diagrams of an example of a device that includes an array and an example of a method.

FIG. 5 shows an example of the array 400 where a user may trace a stroke across the surface 381; noting that the size and/or shape of the array 400 may be selected as desired, from covering the entire surface 381 or one or more portions of the surface 381. FIG. 5 also shows an example of a method 500 that includes a detection block 510 for detecting input and a render block 520 for rendering output responsive to detection of the input.

As an example, a user's finger may cause one or more of deformation of material (e.g., a shell material, a piezo component material, a membrane material, etc.) and a change in air pressure. For example, consider a resilient shell with openings where the user's finger causes membranes of speakers to move due to air pressure changes as the user deforms the resilient shell while covering one or more openings in the resilient shell. In such an example, the array 400 can include LEDs that can respond to such membrane movements by illuminating. As shown in FIG. 5, the user's finger can draw a shape where LEDs can maintain the shape via illumination. In the example of FIG. 5, the non-illuminated openings are not shown in the lower right such that the shape can be more readily illustrated via illuminated openings (filled circles).

In the example of FIG. 5, the array 400 may be suitable for taking notes such that the user remembers a task and/or to communicate a message to another. As to the latter, consider a user scribbling "lunch?" on the surface 381 and then holding up the device 200 such that another person can see the scribbled message. Or, for example, consider a user scribbling "back in 10" and leaving the device 200 at her desk such that people know that she's expecting to return in 10 minutes. In such an example, consider a timer where a clock can be illuminated to show how many minutes are left and/or the time the user scribbled the message.

Figure 6:
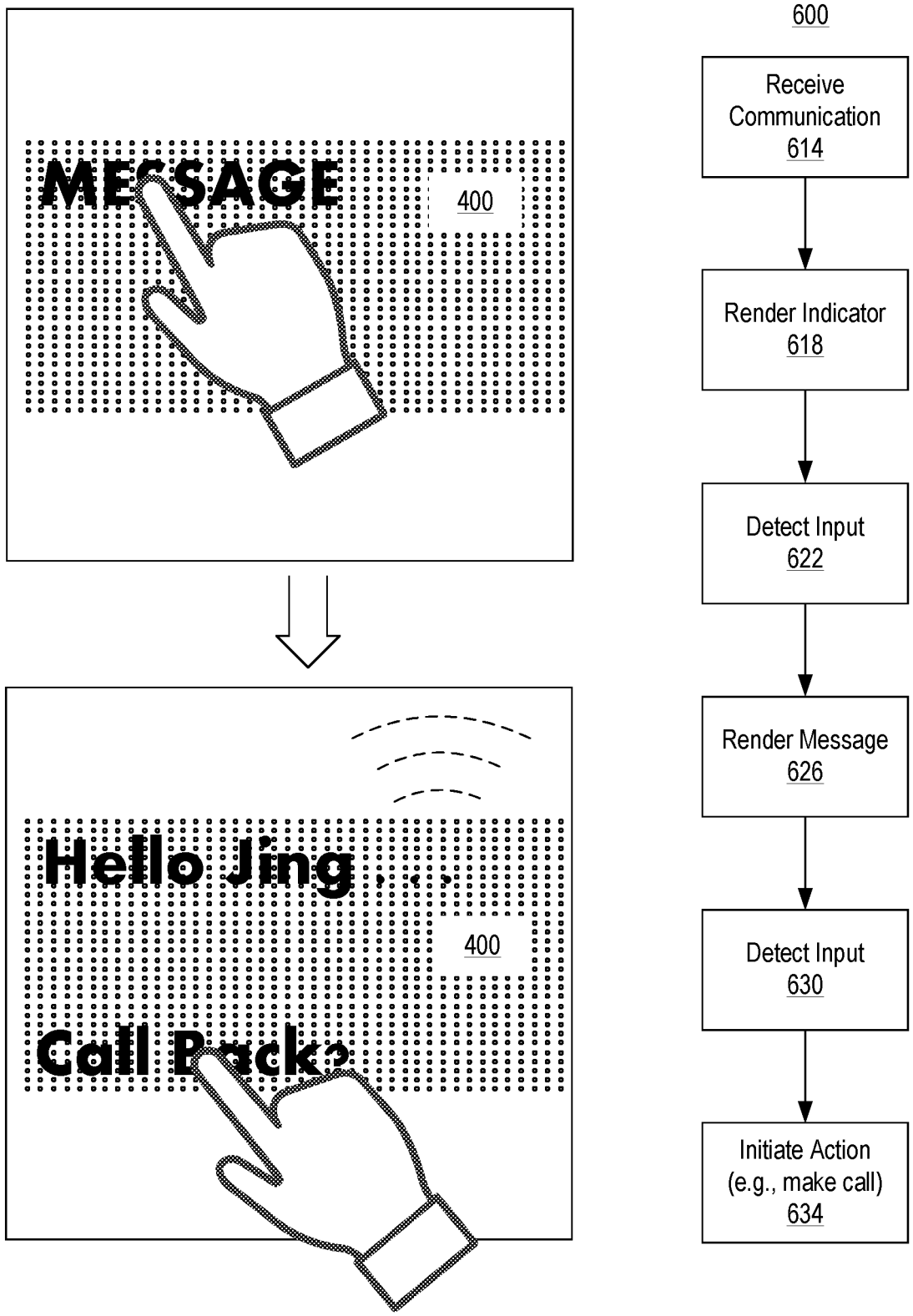
FIG. 6 is a series of diagrams of an example of a device that includes an array and an example of a method.

FIG. 6 shows an example of the array 400 where a message is indicated, as may be formed via illumination of a number of LEDs. In such an example, a user may activate the message, for example, using touch, a voice command (e.g., where the array includes one or more microphones), etc. As shown, in response, the message may be rendered using LEDs and/or using speakers. For example, a user may have multiple options including visual and audio rendering. As explained, a speaker may be utilized for one or more purposes, which can include touch sensing and audio rendering. In the example of FIG. 6, the array 400 renders "Call Back?", which may be triggered via a touch, a voice command, etc. As an example, the array 400 may include one or more microphones and one or more speakers such that it can operate as akin to a phone. In such an example, the array 400 may include one or more electronic components with one or more membranes that may be selectively utilized as a microphone or a speaker. For example, consider an array of 10 membrane circuits where 8 operate collectively as a speaker and 2 operate collectively as a microphone.

FIG. 6 also shows an example of a method 600 that includes a reception block 614 for receiving a communication (e.g., via wire, wirelessly, etc.), a render block 618 for rendering an indication using the array 400, a detection block 622 for detecting input using the array 400, a render block 626 for rendering a message using the array 400, a detection block 630 for detecting input responsive to the message, and an initiation block 634 for initiating an action responsive to the detection of the input (e.g., initiating a call, etc.).

Figure 7:
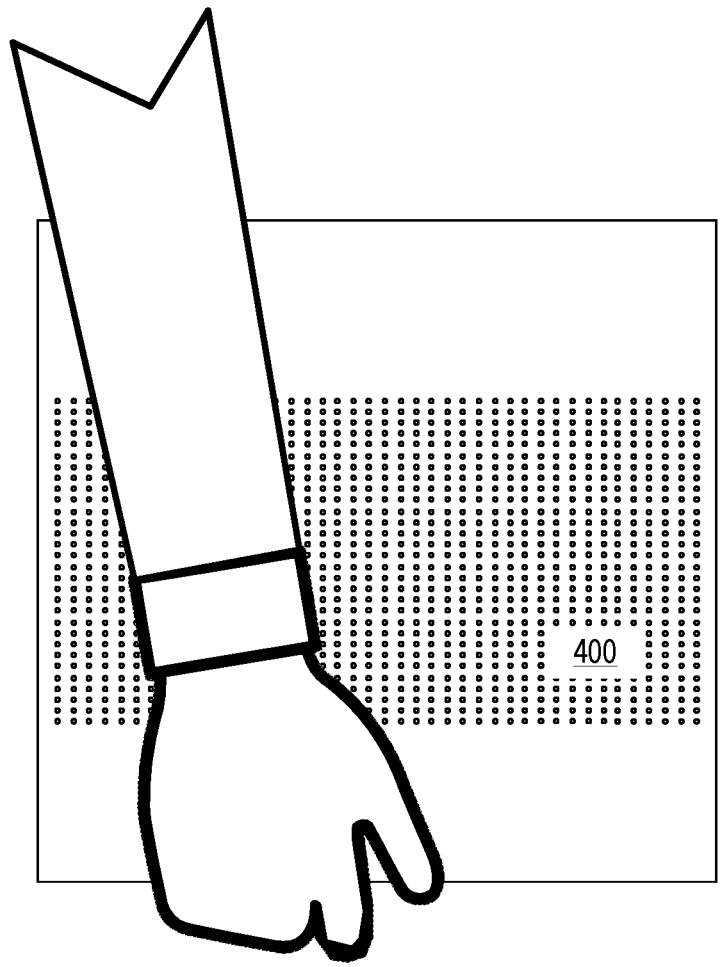
FIG. 7 is a diagram of an example of a device that includes an array and an example of a method.
Figure 7:
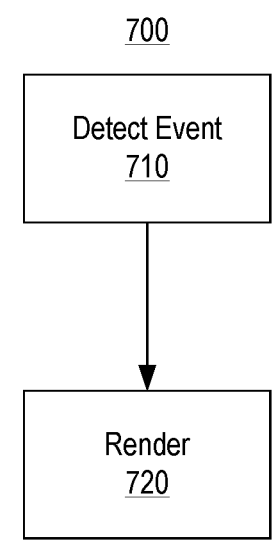

FIG. 7 shows an example of the array 400 that may operate as a haptic array. For example, consider a user carrying the device 200 where the device 200 includes or is operatively coupled to communication circuitry (e.g., a SIM chip, a WiFi chip, a BLUETOOTH chip, etc.). In such an example, upon receipt of a communication signal, the array 400 can include electronic components that can be activated in a manner such that the user can feel them. For example, consider pulsing a number of speakers at a low frequency that is relatively inaudible yet can be sensed by the user's hand and/or forearm. In such an example, the speakers can serve a purpose that is other than rendering of music, rendering of speech, etc. As explained, speakers may be suitable for performing one or more types of actions. And, where the array 400 includes multiple speakers, one or more of the speakers may be selectable for performing a particular action (e.g., depending on purpose, task, amount of battery power available, etc.).

FIG. 7 also shows an example of a method 700 that includes a detection block 710 for detecting an event and a render block 720 for rendering output responsive to detection of the event. For example, consider a timed event (e.g., a calendar event), a communication event, a device related event (e.g., low battery power, closing down, etc.), etc., where the array 400 can render one or more types of output, which may include a physical, haptic type of output such that a user can be alerted as to the detection of the event.

Figure 8:
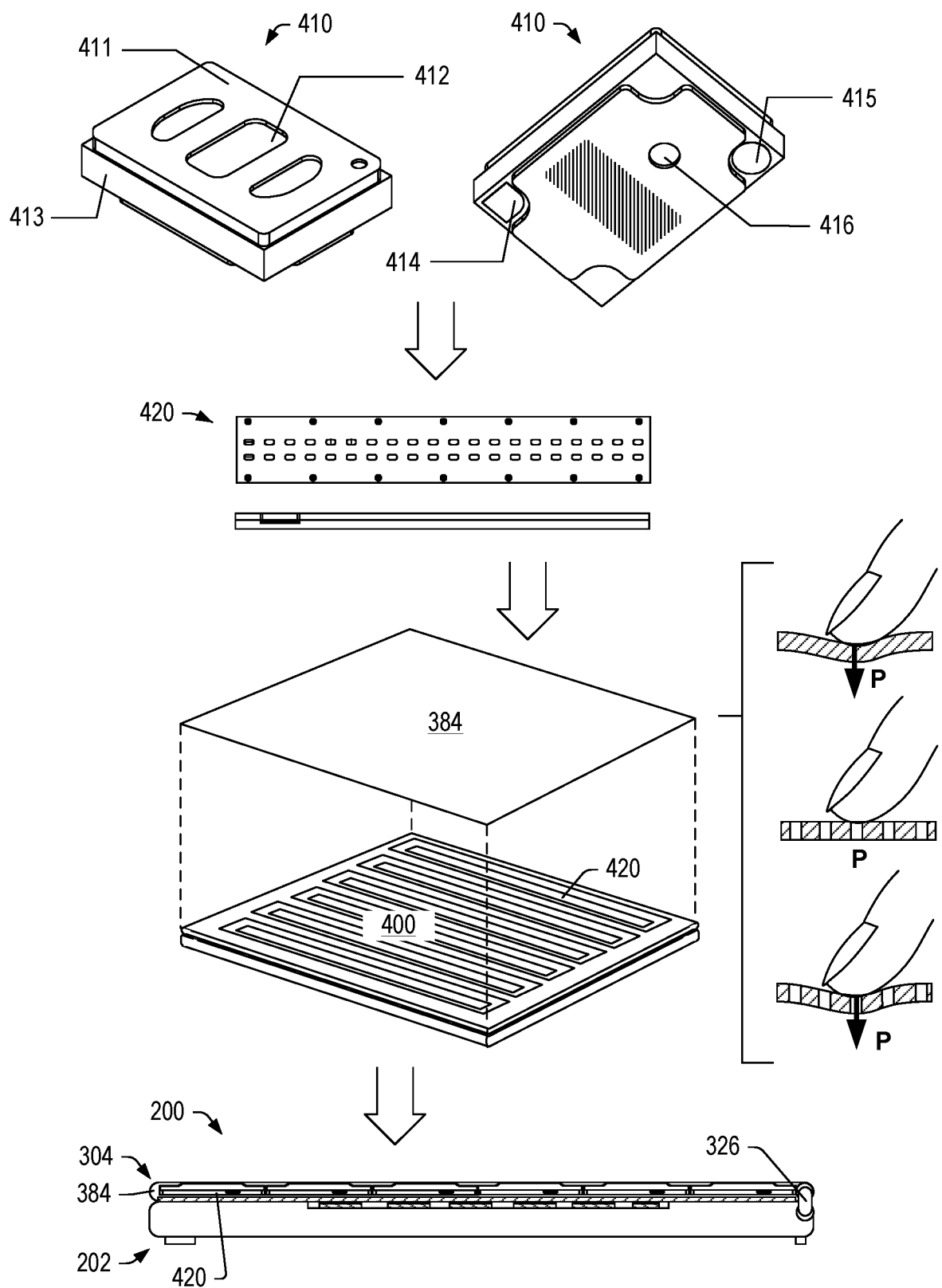
FIG. 8 is a series of diagrams of an example of an electronic component, an example of an array and an example of a device.

FIG. 8 shows an example of an electronic component 410 that can form an array 420 where multiple instances of the array 420 may form a larger array such as the array 400. As shown, the electronic component 410 can include a cover with one or more opening 411, a membrane 412, a ring 413, electronic contacts 414 and 415, and a backport 416. The electronic component 410 can be a transducer that can convert an electrical signal to movement and/or movement to an electrical signal. For example, the electronic component 410 can be a microphone, a speaker, a haptic actuator, a debris cleaner, etc.

As shown, the array 420 can include a series of the electronic components 410, which may be formed as a relatively thin assembly (e.g., less than 10 mm thick). As shown, a plurality of the arrays 420 can be positioned to form the array 400 as a larger array where, for example, a shell 384 can be positioned over the array 400 where the shell may or may not include one or more openings. As mentioned, a shell may be made of a resilient material such that it can be elastically deformable via human touch. In such an example, resilience may be imparted by material properties and/or voids, which may be openings.

In FIG. 8, the shell 384 is shown as having one or more types of characteristics. For example, it may be a solid, resilient shell that can be deformed in response to human touch to cause a pressure that can be detected, it may be rigid with openings such that closing of an opening or openings can be detected (e.g., via air pressure, etc.), or it may be resilient with openings where one or more types of physical phenomena can be utilized for detection (e.g., pressure due to deformation, pressure due to air, pressure due to deformation and air, etc.).

As an example, a shell may be an external shell that includes perforations where such perforations may be classified as microperforations. As an example, a microperforation may be an opening with a maximum dimension that is less than approximately 5 mm. For example, consider an external shell that includes perforations that are less than approximately 2 mm or less than approximately 1 mm. In various instances, as the maximum dimension (e.g., diameter, etc.) decreases, the viewing distance at which the microperforations are discernable decreases in that a viewer must generally be closer to the material having the microperforations to see the microperforations. Thus, an external shell of a computing device may appear to be without microperforations at a viewing distance of approximately 1 m. As an example, consider a line of microperforations of approximately 0.8 mm in diameter with a density of one microperforation per 2.3 mm. In such an example, lines of microperforations may be offset, aligned, etc. As an example, microperforations may be arranged in one or more patterns (e.g., lines, circles, ovals, etc.). As an example, microperforations may be sized, shaped, arranged, etc., to provide acoustic characteristics. As an example, an array may include different sized microperforations. As to a minimum size of a round or circular perforation, it may be approximately 5 microns. As an example, a computing device can include a microperforated array assembly where mircorperforations can include microperforations in a range from approximately 5 microns to approximately 2000 microns (e.g., approximately 2 mm) or, for example, from approximately 100 microns to approximately 1500 microns.

As an example, microperforations may be formed via one or more techniques. For example, consider laser forming of microperforations. As an example, a method can include defining a diameter and a spacing of microperforations for one or more purposes (e.g., for transmission of light, transmission of air, etc.). Depending on such parameters and material of the substrate (e.g., a layer, a shell, etc.), an appropriate type of laser, power and optics may be selected where laser operational parameters may be optimized (e.g., power, pulse, frequency, separation, etc.). As an example, a quality control process can include performing an inspection using scanning electron microscopy (SEM), for example, to determine quality of microperforations.

As an example, a substrate for mircoperforating may be a metallic substrate, a polymeric substrate, a ceramic substrate, a graphite substrate, a composite substrate, etc. As an example, a method can include microperforating a polymeric material, which may be rigid or resilient. As explained, openings in a material such as a polymeric material may make the material resilient and/or more resilient. In various instances, a resilient material that is microperforated may be less amenable to cracking than a rigid material that is microperforated as microperforations can in some instances degrade material strength in a manner that increases risk of cracking.

In the example of FIG. 8, the device 200 can include the array 400 as covered by the shell 384, which may be a protective shell. In such an example, the array 400 may function as a speaker or speakers. For example, consider a left side of the array 400 functioning as a left channel speaker and a right side of the array 400 functioning as a right channel speaker. As an example, various electronic components in the array 400 may be selectable to function as a channel or a multichannel audio system.

As an example, the arrays 420 may differ. For example, consider electronic components that differ in size, which may correspond to differences in frequency response. In such an example, the array 400 may include a sub-array that has a low-range frequency response that can function as a bass audio channel, a sub-array that has a mid-range frequency response that can function as a mid-range audio channel and a sub-array that has a high-range frequency response that can function as a tweeter channel. In such an approach, the device 200 can include multichannel drivers capable of delivering an enhanced user audio experience from a housing where the housing can also include one or more of a display panel, a keyboard, etc. Through utilization of MEMS sized electronic components that can be arranged in one or more arrays, functionality of a housing may be extended, which may provide for excluding one or more types of components from being housing within a housing (see, e.g., the device 200 of FIG. 2 and FIG. 3) where the speaker assembly 216 occupies space of the keyboard housing 202. Where speakers are present in a thin layer of a housing such as the display housing 304, the keyboard housing 202 may be made thinner and/or one or more other components may be increased in size (e.g., more memory, more processors, more battery capacity, etc.).

As explained, an electronic component may operate as an air mover for one or more purposes. As shown in FIG. 8, the electronic component 410 can include a backport 416 that can facilitate movement of the membrane 412. For example, without the backport 416, movement of the membrane 412 may cause an increase or a decrease in pressure within a space of the electronic component 410. As such, with the backport 416, movement of the membrane 412 causes air to move into or out of the space via the backport 416. As an example, such air may be utilized for purposes of heat transfer, for example, to help cool a device. While the amount of air moved by an individual electronic component may be relatively small, where 10 or more electronic components are utilized, the amount of air moved may be sufficient to improve heat transfer. For example, consider the array 420 as including 40 speakers and the device 200 including at least three of the arrays 420 such that 120 speakers are present where movement of the membranes 412 of the 120 speakers can move an amount of air that helps to transfer heat.

As an example, the array 420 can include one or more features of the MEMS speaker array Harpalkyke UY-R2010 of USound GmbH. Such an array can include 40 speakers that are electrically connected in parallel; noting that, as an example, an array of speakers may be otherwise connected, for example, into channels. The Harpalkyke array has a back volume of 100 cubic millimeters per speaker, with dimensions of 200 mm×32 mm×7.6 mm.

As an example, an array may be manufactured to be thinner than 7.6 mm. For example, consider the electronic component 410 as having dimensions of approximately 6.7 mm×4.7 mm×1.58 mm. As an example, the electronic component 410 can include one or more features of the MEMS speaker Adap UT-P 2019 or UT-P 2017 of USound GmbH. As an example, an array may include one or more features of an array such as the Dione Maxi UY-R3020 array of USound GmbH, which can be matched with an external amplifier to drive the MEMS speakers of the array. The Dione Maxi UY-R3020 array can include 20 speakers with a length of approximately 238 mm, a width of approximately 12 mm and a thickness of approximately 4 mm. In such an example, each of the 20 speakers can be an Adap UT-P 2019 housed in a pocket and coupled to a flexible substrate (e.g., a flexible PCB).

As an example, microperforations may be arranged such that a number of microperforations are provided for an individual electronic component. For example, the aforementioned dimensions of the example electronic component 410 are 6.7 mm×4.7 mm where the electronic component 410, itself, includes three openings in the cover 411. As shown, the area of the openings may be approximately 5 mm×approximately 3 mm (e.g., approximately 15 mm²). Where a center to center spacing of microperforations is approximately 1 mm, a portion of an array of microperforations for the particular electronic component 410 may include approximately 15 microperforations (e.g., consider a 5×3 array of microperforations) or more directly above the electronic component 410.

As an example, an array of electronic components may be disposed in one housing and circuitry operatively coupled to the array disposed in another housing. For example, consider an array disposed in a display housing with one or more types of circuitry disposed in a keyboard housing where the display housing and the keyboard housing form a device (e.g., as may be coupled via one or more hinge assemblies).

Figure 9:
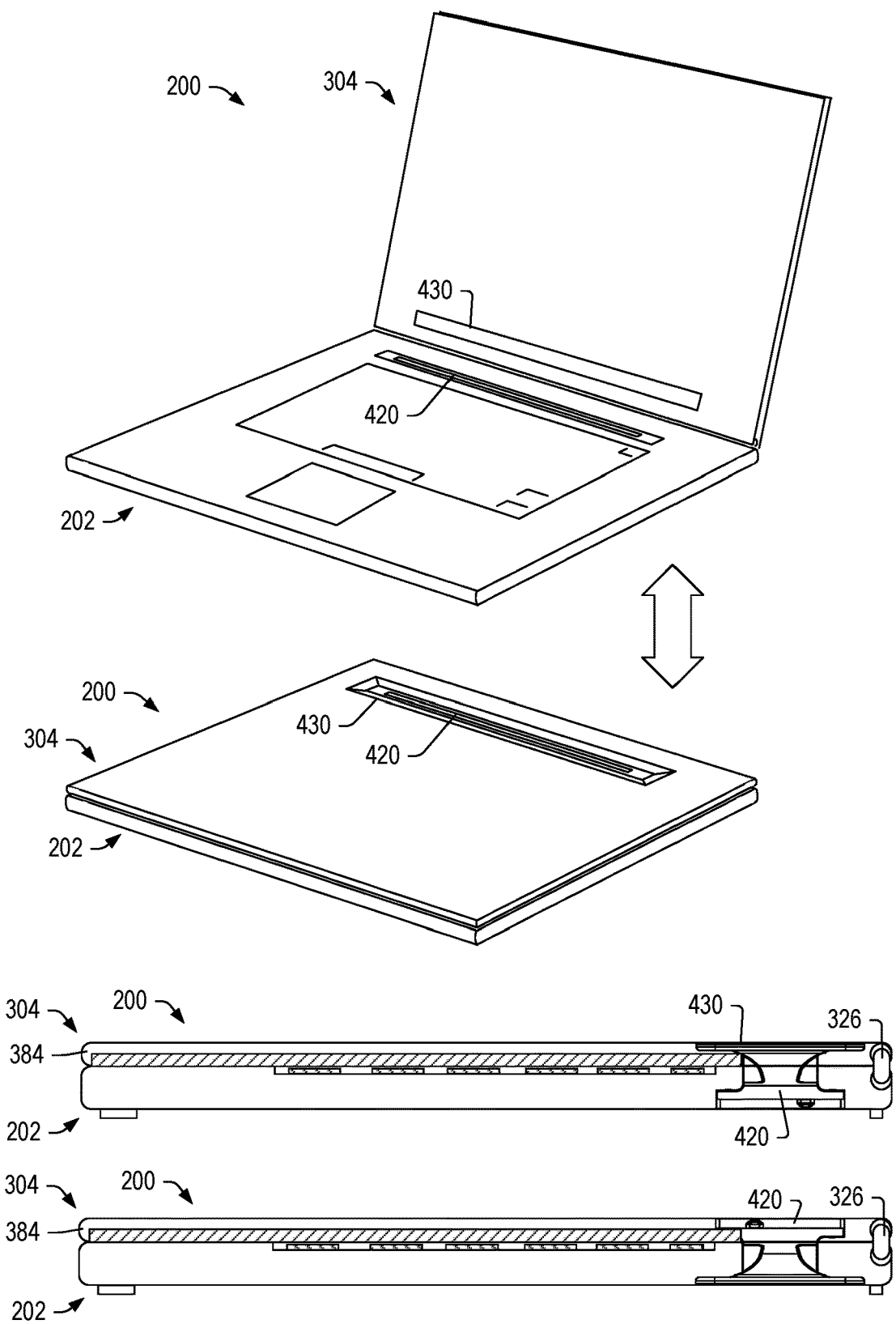
FIG. 9 is a series of diagrams of an example of a device that includes an array.

FIG. 9 shows an example of the device 200 as including the array 420, which may be in the display housing 304 or in the keyboard housing 202. As shown, the device 200 can include a corresponding horn or horns 430 that may be part of the keyboard housing 202 or part of the display housing 304. In such an example, where the device 200 is a clamshell device, in a closed orientation, the horn 430 can align with the array 420 such that the horn 430 can help to define acoustic performance of the array 420.

Figure 10:
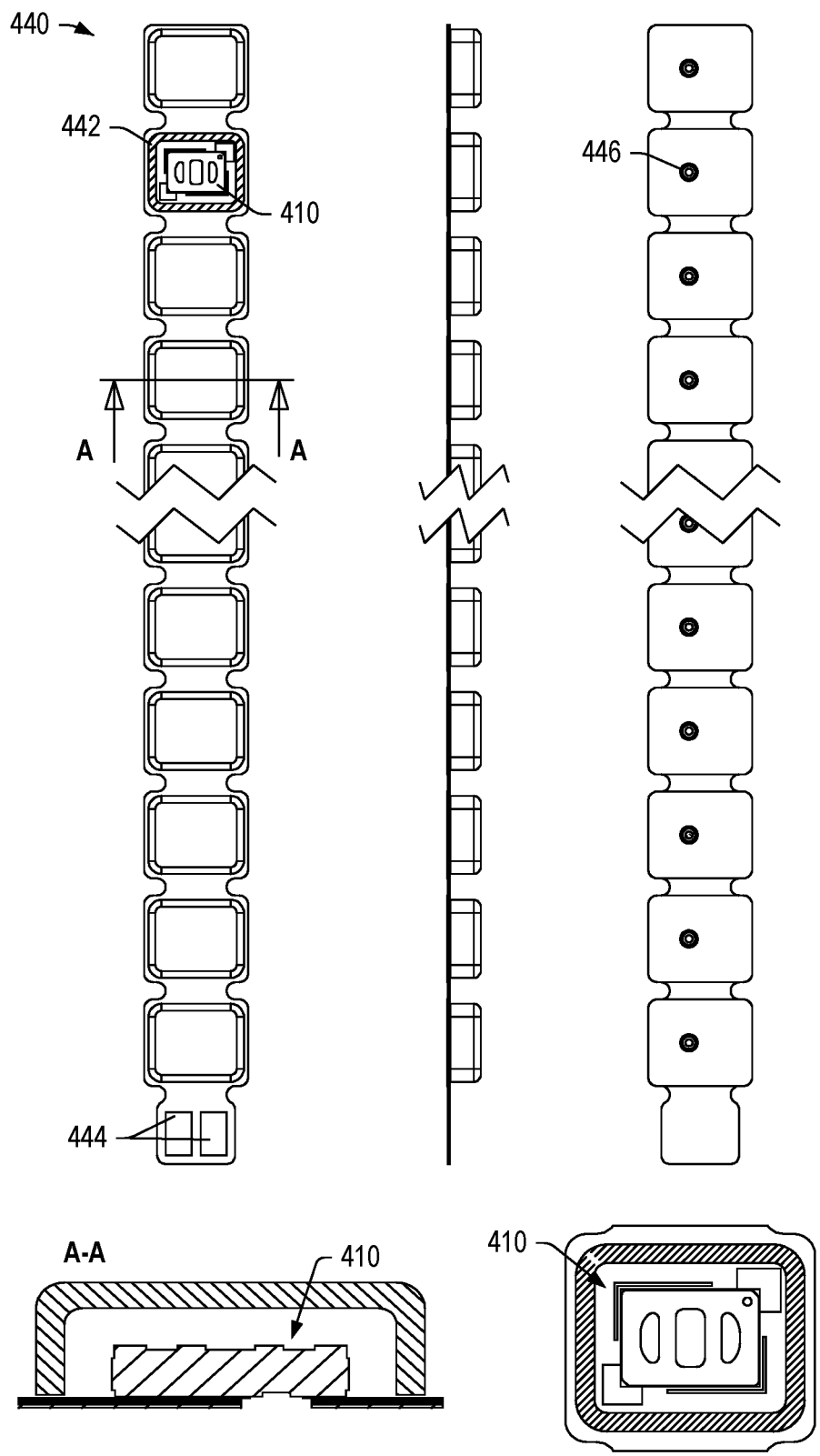
FIG. 10 is a series of diagrams of an example of an array.

FIG. 10 shows an example of an array 440 that includes a plurality of the electronic components 410, which may be arranged in a linear manner, optionally on a substrate that is flexible (e.g., elastically deformable, etc.). In the example of FIG. 10, the array 440 includes a housing material 442 that can include a series of ports 446 and one or more conductors with electrical contacts 444, which can provide for electrical coupling of the electronic components 410 to operate responsive to a common signal. As an example, a multiplexer or other circuitry may be included such that the electronic components 410 of the array 440 may be selectively sampled, selectively actuated, etc. For example, the electrical contacts 444 may be a series of contacts that can be addressable.

As an example, in the array 440, the electronic components may be the same or they may differ. As an example, a battery or batteries may be included in the array. As an example, the array 440 may be self-contained in that it may be capable of operation independent of other circuitry of a computing device. As an example, the array 440 may be capable of receiving input and rendering output responsive to the input. As an example, the array 440 may include an interface that can output information to other circuitry of a computing device to instruct operation of the computing device and/or may include an interface that can receive information from other circuitry of a computing device to instruct operation of the array 440.

As an example, an I2C and/or an I2S type of bus architecture may be utilized for one or more types of electronic components in an array. An I2C interface can be a two wire serial data connection interface with a serial data (SDA) line and serial clock (SCL) line. Data rates can be in excess of 100 Kbps (e.g., 400 Kbps, 1 Mbps, 3.4 Mbps, etc.). An I2C approach may provide for synchronous communication (e.g., consider a common clock signal). An I2S approach can utilize separate data and clock signals and include a word-select line (WS), a clock line (SCK) and a multiplexed serial data line (SD). As an example, a UART and/or a USART approach may be utilized. As an example, an array may include one or more of a clock generator, input and output shift registers, transmit/receive control, read/write control logic, transmit/receive buffers, system data bus buffer, first-in, first-out (FIFO) buffer memory, a DMA controller, etc.

As an example, an array may include or be operatively coupled to one or more DC boost converters, one or more amplifiers, etc. (e.g., consider one or more of a Texas Instruments TPS61046, LM 48580, etc.). As an example, an array may include one or more digital signal processors (DSPs) and/or be operatively coupled to one or more DSPs.

As an example, a laptop clamshell computer can be defined with respect to an A, B, C and D notation where the A side is the top cover, the B side is the display side opposite the A side, the C side is the keyboard/trackpad side, and the D side is the base side, opposite the C side.

In various computing devices, sound output is generally optimized to be user facing, generally tuning the speakers located in the C and D covers or in a moving element such as a speaker bar implementation (e.g., coupled to one or more hinge assemblies, etc.).

As explained, one or more electronic components may be Micro-Electro-Mechanical Systems (MEMS) components. For example, the electronic component 410 can be a MEMS speaker. Through use of such electronic components, a computing device can conserve space, utilize space differently, etc. As explained, through use of an array or arrays, various types of functionality may be realized, which can include functionality beyond that of the speaker assembly 216.

As an example, an array of speakers may be utilized to optimize user experience, which may be for more than one listener or to better isolate sound emissions to one individual.

As explained, one or more of different types of transducers may be utilized, which can include, for example, one or more of different types of micro transducers that can be arranged into one or more arrays.

Figure 11:
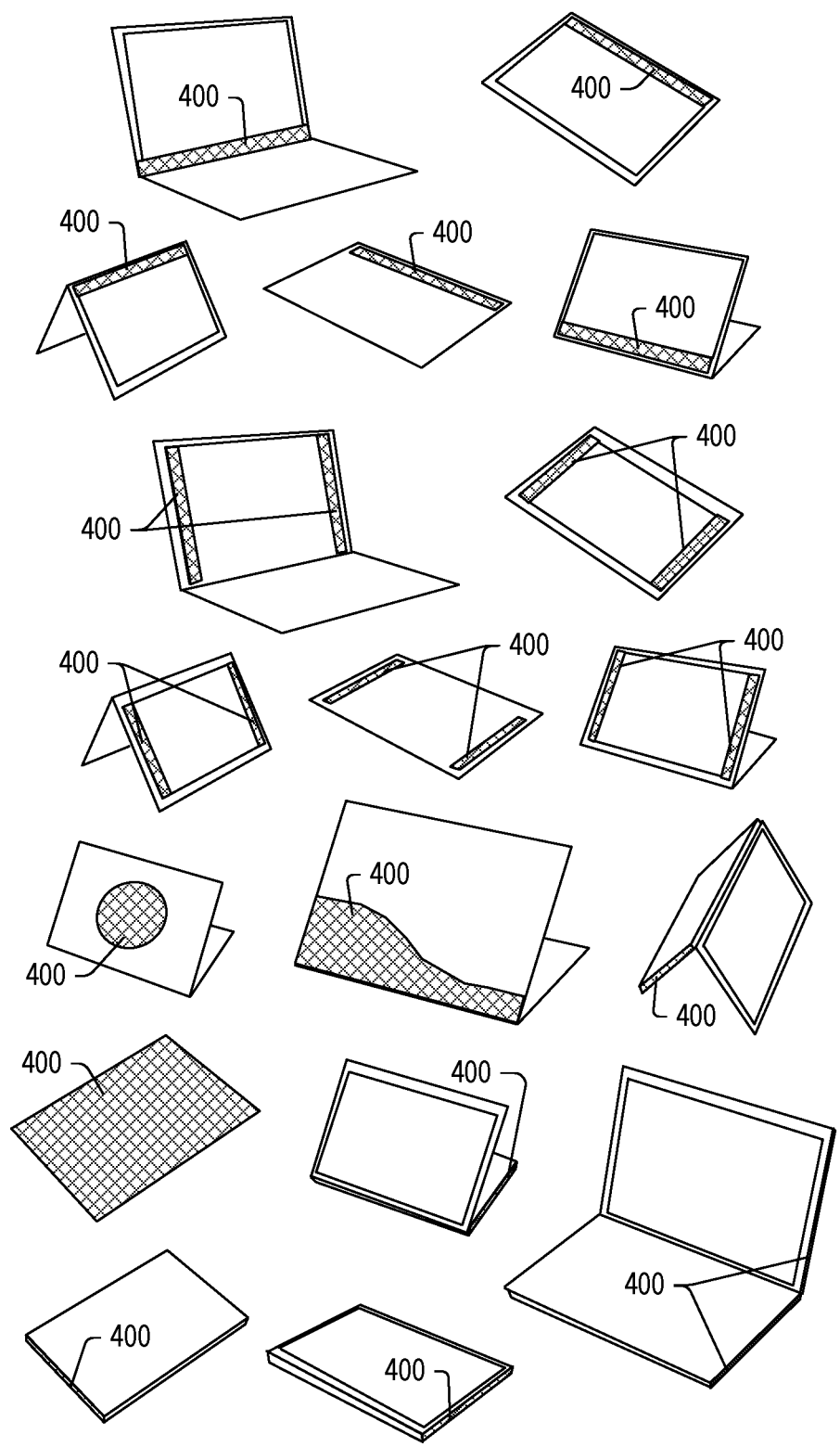
FIG. 11 is a series of diagrams of examples of devices.

FIG. 11 shows various examples of one or more arrays 400 as included in various computing devices. For example, the array 400 may be implemented as one or more arrays with respect to an A side, a B side, a C side and/or a D side. As shown, one or more arrays may be arranged with respect to an edge, for example, an edge between an A side and a B side and/or an edge between a C side and a D side.

As an example, an array or arrays may be triggered when a computing device is in a particular orientation. For example, consider one or more of the orientations 101, 103, 105, 107 and 109 of the example computing device 100 of FIG. 1. As an example, an orientation sensor (e.g., accelerometer, gyroscope, proximity sensor, etc.) may be utilized to determine an orientation and, in response, control operation of one or more arrays (e.g., activate, deactivate, etc.).

Where, for example, an array of an A side includes speakers, when a clamshell computing device is in a closed orientation (e.g., display facing a keyboard), speakers such as those of the speaker assembly 216 in FIG. 2 may be suboptimal by comparison.

As to device related interactions that can be dependent on audio input and/or output (e.g., audio I/O), such as voice computing and communications, through use of one or more arrays, audio hardware may be more fully optimized to deliver a premium user experience. As mentioned, consider control of one or more channels (e.g., left, right, bass, surround sound, etc.). As to a surround sound experience, consider an example where a user's computing device is to be utilized in a conference room where a group of individuals may be seated about a conference room table. In such an example, an array or arrays of speakers may be operated in a surround sound mode that provides for emission of sound that can more fully reach the individuals in the group.

As explained, audio I/O can be lacking for convertible computing devices. For example, when the lid is closed, there may be no speakers that are user facing. Further, consider a microphone, which may be part of a sub-assembly, mounted on a B side such as a bezel region about a display. When in a closed orientation, the microphone or microphones may be suboptimally positioned. In contrast, as mentioned, one or more microphones may be arranged on the A side where, for example, one or more electronic components may be capable of functioning as two way transducers (e.g., as a microphone and as a speaker).

In various tent orientations, issues may exist with audio input and/or output. As explained with respect to the various examples of FIG. 11, one or more arrays may provide for improved tent orientation audio input and/or output.

As explained, an array may be embedded in a housing such as a display housing, a keyboard housing, a tablet housing, etc. Such types of housings may provide for one or more types of form factors, which may fold or have various types of shapes and/or movements, some of which may be beyond those available under constraints of keyboard housing speaker assemblies such as the speaker assembly 216 of FIG. 2.

As explained, various MEMS electronic components can be transducers that may be located adjacent to a display, along one or more bezels, along one or more edges, under a keyboard, integrated into a shell, etc.

As an example, an array of discrete electronic components can provide for one or more types of interactions that may be integrated complimentarily with color, material and/or finish (CMF) of a computing device. As explained, a transducer can provide for sensing, audio, user interface rendering, etc., which may integrate more seamlessly with CMF while giving users familiar and improved methods of interaction. As explained, a shell with openings may retain a relatively clean appearance and/or a shell with resiliency may retain a relatively clean appearance where, in either or both instances, the shell can be an activatable surface, for one or more purposes.

Figure 12:
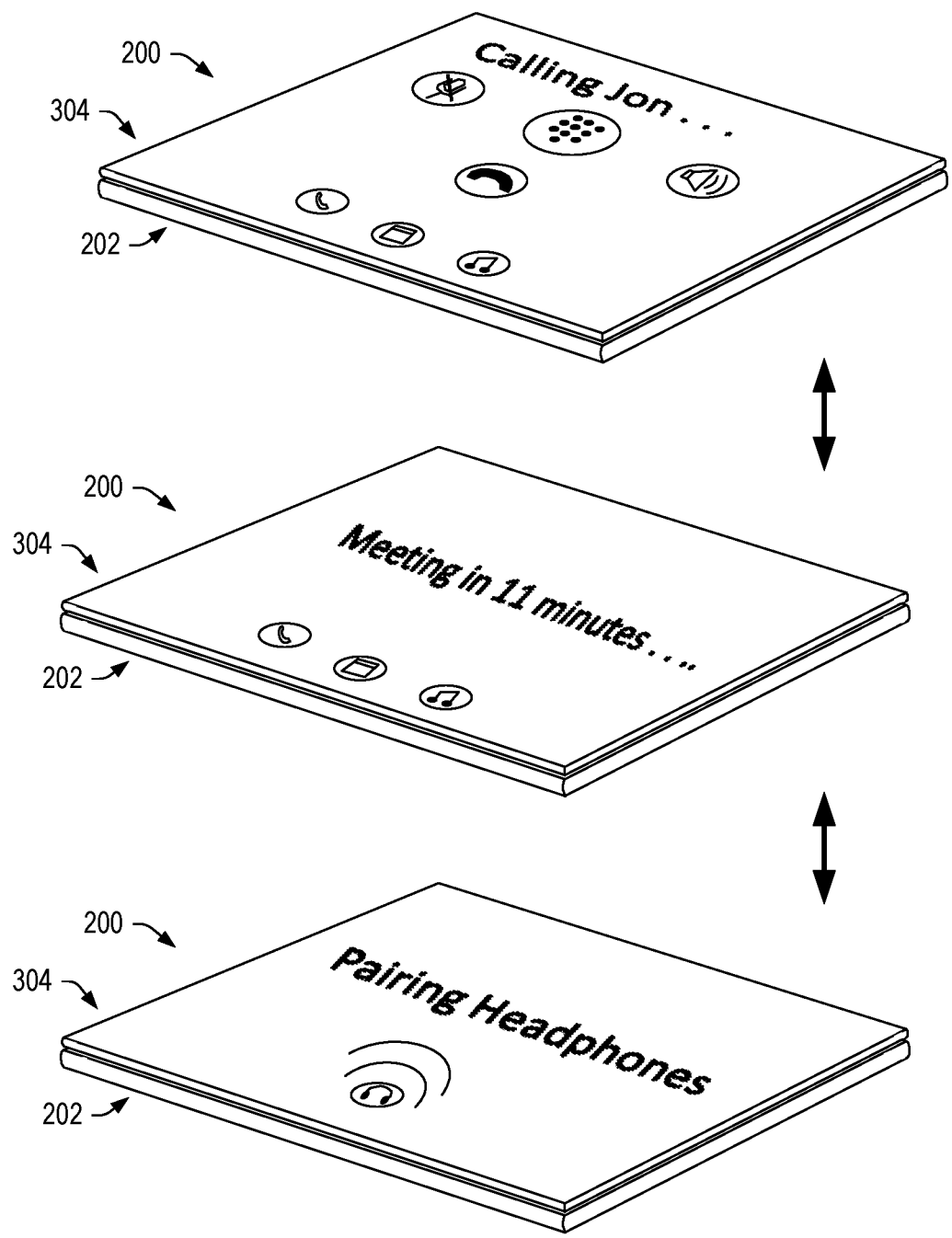
FIG. 12 is a series of diagrams of an example of a device in example operational scenarios.

FIG. 12 shows some examples of how an A side may be utilized with one or more arrays of electronic components, which can be or include MEMS electronic components that can be transducers. As shown, the computing device 200 can render communication information and functionality to the A side, can render notices to the A side, can render pairing information to the A side, etc. In such examples, the functionality of the computing device 200 can be extended, particularly when the computing device 200 is a clamshell computing device that is in a closed orientation (e.g., closed clamshell orientation where the A side may be viewable to a user).

As an example, functionality may include one or more of sound, touch, lighting, sterilization, special effects, rendering of information, input of security information (e.g., fingerprint, touch gesture, etc.), etc.

As explained, an A side may provide for touch interaction where lighting components may help to guide and/or respond to such interactions.

As explained, where a shell is utilized on an A side, the shell may provide for protection of one or more electronic components in one or more arrays. In such an approach, a user may not have to worry about damage such as if the A side were an unprotected LCD, OLED, e-ink or other type of display that may be quite susceptible to damage if present on an A side (e.g., A cover).

As explained, for convertible computing devices with modes like closed lid or tablet mode, various components like display, buttons, and audio may be blocked or non-interactive. Where an array or arrays are present, functionality may be available and/or extended.

As explained, a computing device can include one or more of audio, display, and touch via one or more arrays, which may be integrated in a manner that comports with a CMF strategy, which being able to improve thinness, lightweightedness, etc.

As explained, an electronic component may provide for haptic notification and/or feedback. As mentioned, a speaker or other type of transducer may be operable at a frequency (e.g., low, high, etc.), which may be generally outside the range of hearing of an individual (e.g., less than about 20 Hz and/or greater than about 20 kHz). Such types of transducers can make one or more surfaces interactive.

As an example, an array or arrays may provide for one or more phygital button presses, swipes, and gestures. As explained with respect to the various examples of FIG. 11, electronic components may be embedded into static surfaces like the A side, a palm rest of the C side, a display bezel of the B side, and/or one or more other surfaces, which may be of limited volumetric space.

By complimenting traditional components with MEMs speakers along the bezel of a display or otherwise arrayed may provide for fuller and/or more user-directional sound. As mentioned, one or more types of materials such as, for example, e-textiles, woven, knit, or acoustically optimized materials like a microperforated CMF shell can be placed over an array of transducers. In such an approach, an array may be relatively hidden such that an individual may not notice a difference unless closely inspected to reveal microperforations (e.g., relatively small openings, etc.).

As an example, one or more user interfaces, dynamic displays, etc., may appear and disappear on seemingly solid surfaces like the A side or a palm rest of the C side. As an example, an array or arrays may leverage miniaturization display-tech like one or more of micro-LEDs, printable LEDs and e-textiles. As an example, one or more types of display technologies may be embedded onto a surface, emitted through microperforations, or placed underneath woven/knit/micro perforated materials.

Figure 13:
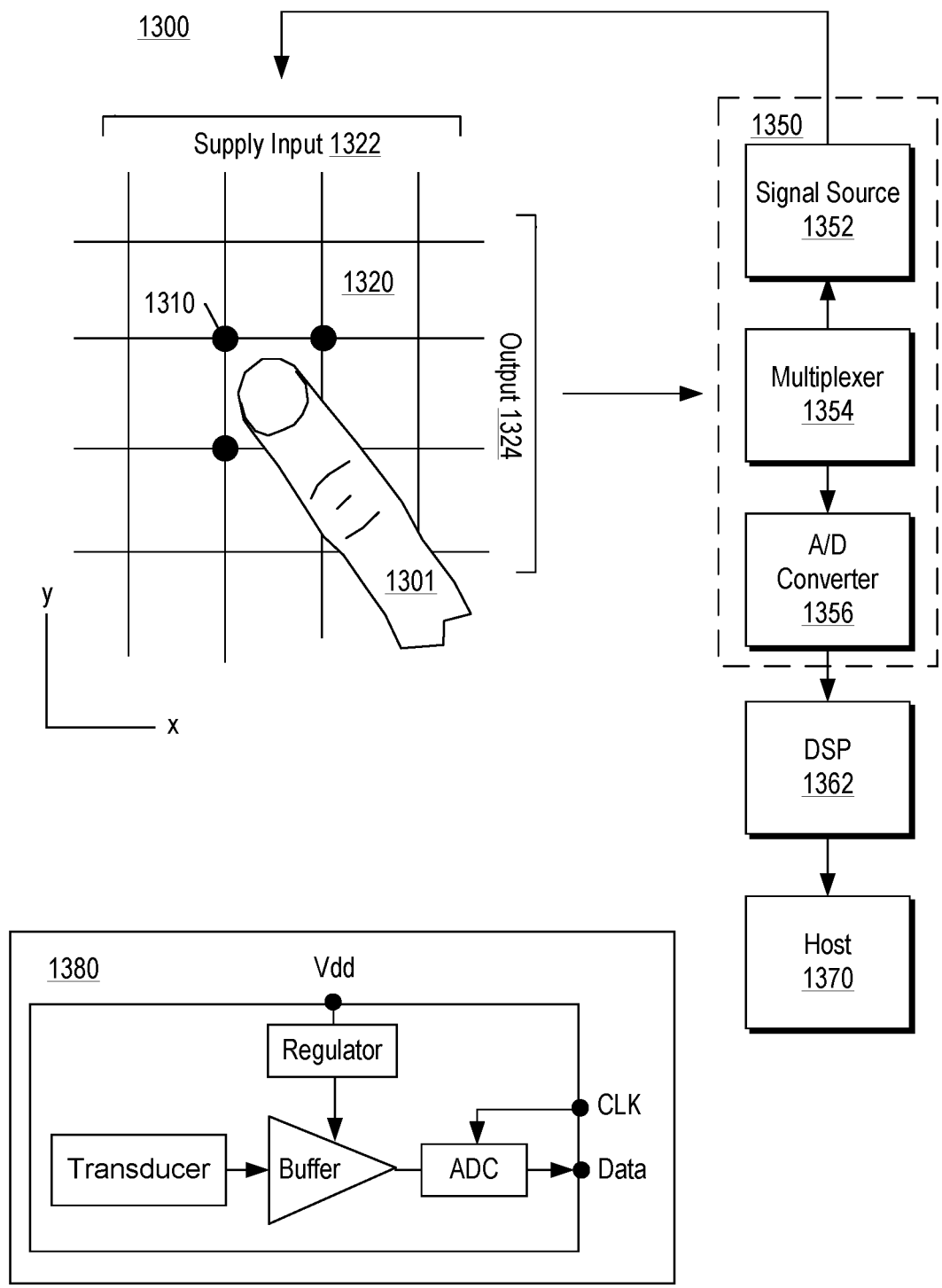
FIG. 13 is a series of diagrams of examples of circuitry and an example of a method.

FIG. 13 shows some examples of circuitry 1300 and 1380 and an example of a method 1350. As shown, an array 1320 can include electronic components 1310 that are operatively coupled to supply input 1322 and output 1324 circuitry. As shown, the method 1350 can include a signal source block 1352 for supplying power and/or data to the array 1320, a multiplexer block 1354 for addressing, an optional analog to digital converter block 1356 where analog signals, if present from one or more electronic components of the array 1320, can be converted to digital form, a digital signal processing (DSP) block 1362 that can process digital output and a host block 1370 that can provide for utilizing output of the DSP block 1362.

As to the example circuitry 1380, as shown, it can receive supply power (e.g., Vdd), a clock signal (CLK) and output data. For example, consider an I2C type of two line approach that includes a clock line and a data line and another line or lines for supply of power (e.g., DV voltage, etc.). In the example circuitry 1380, a transducer can output information to a buffer, which may be supplied with a voltage via a regulator, where output of the buffer may be directed to an ADC that operates according to the clock signal from the clock line to output data via the data line. In the example circuitry 1380, the Vdd, the CLK, and/or the data may be controlled, for example, in response to one or more actions, etc.

As an example, an array can include one or more electronic components that can convert chemical energy to electrical energy. For example, consider a battery as a transducer. As an example, an array can include one or more power sources that may be operatively coupled to or independent of a main battery of a computing device. In such an example, the array can include relatively low power consumption components (e.g., consider MEMS components that can consume a relatively low amount of power). As an example, a lifetime of operation of electronic components of an array may be powerable via one or more non-rechargeable batteries and/or rechargeable batteries. For example, consider a coin-type of battery that can be utilized to power electronic components of an array, which may be in a manner independent of circuitry of a computing device. For example, consider a display housing that includes circuitry that can operate independent of a computing device that includes the display housing. In such an example, the circuitry may be powered using a battery disposed within the display housing.

As an example, an array may include one or more solar cells that can be transducers of light energy to electrical energy. In such an example, one or more electrical energy storage devices may be included that can store harvested energy, for example, to power one or more electronic components of an array.

As an example, a shell can be a shell assembly that includes an array or arrays. For example, a shell assembly may be an A side shell assembly, a B side shell assembly, a C side shell assembly or a D side shell assembly.

In various examples, a shell assembly can include one or more of various types of discrete MEMs or MEMS like components as an array. As an example, many small components may operate akin to one big component. For example, an array of MEMs speakers may act as a single speaker and may possibly act for haptic feedback, as sensors, for example, if one taps on a shell, a pressure wave may cause the speaker membrane to move and generate an electrical signal (e.g., like a strain gauge).

Figure 14:
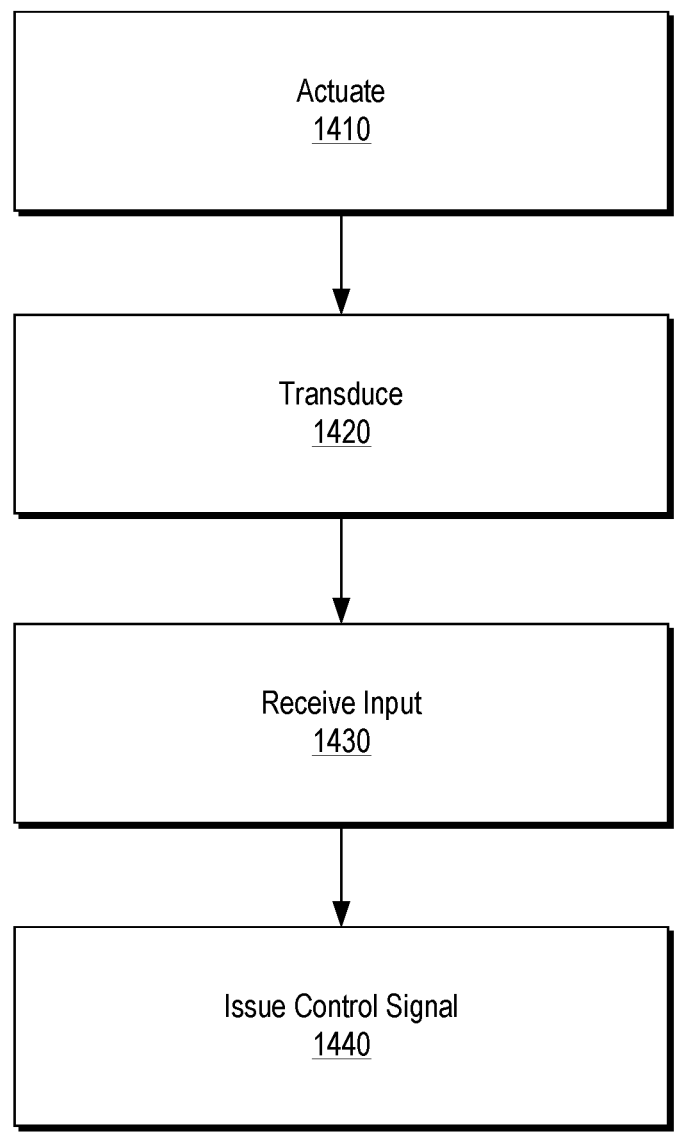
FIG. 14 is a diagram of an example of a method.

FIG. 14 shows an example of a method 1400 that includes an actuate block 1410 for actuating one or more electronic components of one or more arrays, a transduce block 1420 for transducing one or more physical phenomenon, a reception block 1430 for receiving input responsive to the transducing and an issuance block 1440 for issuing a control signal responsive to the receiving input. In such an example, the transduce block 1420 may utilize one or more transducers to generate one or more types of signals for a user such as, for example, a haptic signal, an audio signal, a visual signal, etc.

As an example, a computing device can include a processor; memory accessible to the processor; a display operatively coupled to the processor; and an external shell assembly that includes an array of electronic components, where the array of electronic components includes transducers. In such an example, each of at least some of the transducers can include a membrane. For example, consider a membrane that is a strain gauge membrane and/or a membrane that is a speaker membrane. As an example, where resistance to movement of a membrane changes, an electrical signal may be generated that indicates an amount of resistance (e.g., considered a covered opening or openings, etc., that may increase resistance to movement).

As an example, in a computing device, an array can include transducers that include one or more light emitting diodes. As an example, a light emitting diode may be an ultraviolet radiation emitting diode. In such an example, the UV radiation may be UVC such as, for example, far-UVC.

As an example, an array of electronic components can include one or more batteries where, for example, at least one of the one or more batteries is non-rechargeable and/or at least one of the one or more batteries is rechargeable. As an example, a power supply selector may be operable to supply power via a main rechargeable battery of a computing device or to supply power via another battery, which may be non-rechargeable or rechargeable. In such an example, the power supply selector may operate responsive to one or more conditions where an array of electronic components can be supplied with power, for example, when a processor of the computing device is not supplied with power (e.g., a no power state) or otherwise in a low power state (e.g., a sleep state, a hibernate state, etc.).

As an example, an array of electronic components can include different types of electronic components. For example, consider electricity to light transducers and electricity to mechanical motion transducers. In such an example, the electricity to mechanical motion transducers may be operable as mechanical motion to electricity transducers. As an example, different types of electronic components can include electricity to light transducers and mechanical motion to electricity transducers.

As an example, a computing device can include a display housing for a display, a keyboard housing for a keyboard, and a hinge assembly that operatively couples the display housing and the keyboard housing. In such an example, an external shell assembly can be or include a display housing shell.

As an example, a computing device can include a battery and power circuitry operatively coupled to the battery, a processor and an array of electronic components, where the power circuitry selectively supplies power to the array of electronic components without supplying power to the processor. For example, consider a low or no power state of the processor.

As an example, a computing device can include a battery and power circuitry operatively coupled to the battery, a processor and an array of electronic components, where the power circuitry selectively supplies power to the array of electronic components while supplying power to the processor.

As an example, a computing device can include an array of electronic components that is operable independent of operation of a processor (e.g., a central processor or CPU of the computing device).

As an example, an array of electronic components of a computing device may be operatively coupled to a processor of the computing device. As an example, a computing device can include power circuitry that selectively supplies power to an array of electronic components responsive to a power mode of the processor.

As an example, a power mode or power state of a computing device and/or a processor or processors of a computing device (e.g., CPU or CPUs) may correspond to one or more Advanced Configuration and Power Interface specification (ACPI) states, which can include performance power states (e.g., P states) and processor idle sleep states (e.g., C states); noting that some approaches define global states (e.g., G states). P states can provide a way to scale the frequency and voltage at which the processor runs so as to reduce the power consumption of the processor. C states can be states when a processor has reduced or turned off selected functions. Generally, higher C states turn off more parts of a CPU, which substantially reduces power consumption (e.g., consider a highest C state where a CPU is completely powered off).

As an example, G0 can be working, G1 can be sleeping with S0, S1, S2, S3 (e.g., standby, sleep, or suspend to RAM), and/or S4 (e.g., hibernation or suspend to Disk), G2 can be soft off with S5 where, for example, one or more components may remain powered so a computing device can wake on input (e.g., from a keyboard, clock, modem, LAN, or USB device), and G3 can be mechanical off (e.g., a mechanical off switch. As an example, an array of a computing device may be operable in one or more of the following states and may, for example, be powered using one or more power sources, which may be selected in a state dependent manner. As explained, an array may include its own dedicated power source, which may, for example, be utilized where a computing device may be in a G0, a G1, a G2 or a G3 state. As to G1, G2 and G3 states, these may occur responsive to closing a clamshell computing device where an external shell surface may be active and/or become active, which as mentioned, may be powered by its own dedicated power source in a manner that can depend on the state of the clamshell computing device. As an example, an array may provide for detection of input where such input may be utilized to wake a computing device (e.g., wake on input), for example, as explained with respect to G2 and S5, above.

The term "circuit" or "circuitry" is used in the summary, description, and/or claims. As is well known in the art, the term "circuitry" includes all levels of available integration (e.g., from discrete logic circuits to the highest level of circuit integration such as VLSI, and includes programmable logic components programmed to perform the functions of an embodiment as well as general-purpose or special-purpose processors programmed with instructions to perform those functions) that includes at least one physical component such as at least one piece of hardware. A processor can be circuitry. Memory can be circuitry. Circuitry may be processor-based, processor accessible, operatively coupled to a processor, etc. Circuitry may optionally rely on one or more computer-readable media that includes computer-executable instructions. As described herein, a computer-readable medium may be a storage device (e.g., a memory chip, a memory card, a storage disk, etc.) and referred to as a computer-readable storage medium, which is non-transitory and not a signal or a carrier wave.

Figure 15:
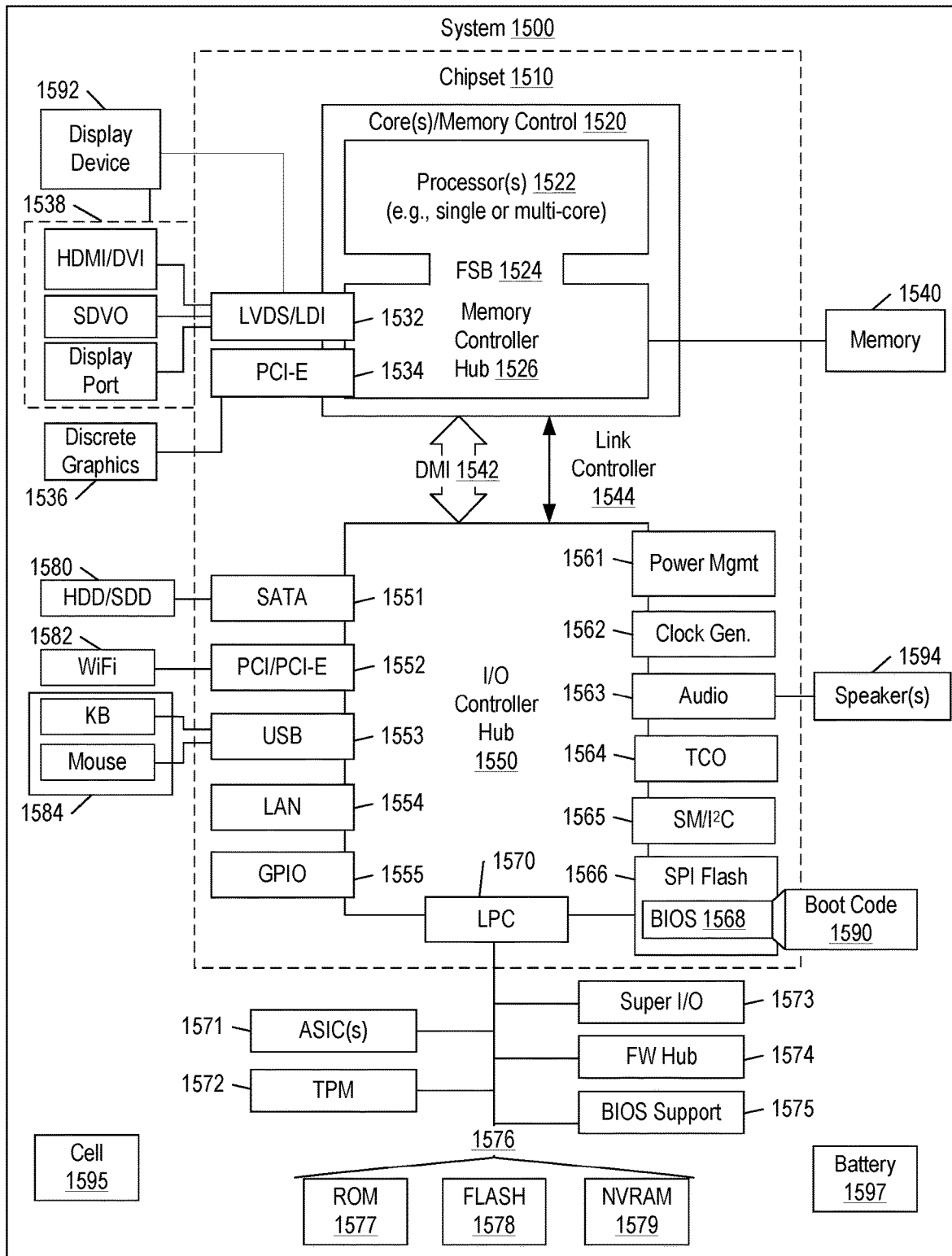
FIG. 15 is a diagram of an example of a system that includes one or more processors.

While various examples of circuits or circuitry have been discussed, FIG. 15 depicts a block diagram of an illustrative computer system 1500. The system 1500 may be a computer system, such as one of the ThinkCentre® or ThinkPad® series of personal computers sold by Lenovo (US) Inc. of Morrisville, NC, or a workstation computer system, such as the ThinkStation®, which are sold by Lenovo (US) Inc. of Morrisville, NC; however, as apparent from the description herein, a system or other machine may include other features or only some of the features of the system 1500. As an example, a system such as the device 100, the device 200, etc., may include at least some of the features of the system 1500.

As shown in FIG. 15, the system 1500 includes a so-called chipset 1510. A chipset refers to a group of integrated circuits, or chips, that are designed (e.g., configured) to work together. Chipsets are usually marketed as a single product (e.g., consider chipsets marketed under the brands INTEL®, AMD®, etc.).

In the example of FIG. 15, the chipset 1510 has a particular architecture, which may vary to some extent depending on brand or manufacturer. The architecture of the chipset 1510 includes a core and memory control group 1520 and an I/O controller hub 1550 that exchange information (e.g., data, signals, commands, etc.) via, for example, a direct management interface or direct media interface (DMI) 1542 or a link controller 1544. In the example of FIG. 15, the DMI 1542 is a chip-to-chip interface (sometimes referred to as being a link between a "northbridge" and a "southbridge").

The core and memory control group 1520 include one or more processors 1522 (e.g., single core or multi-core) and a memory controller hub 1526 that exchange information via a front side bus (FSB) 1524. As described herein, various components of the core and memory control group 1520 may be integrated onto a single processor die, for example, to make a chip that supplants the conventional "northbridge" style architecture.

The memory controller hub 1526 interfaces with memory 1540. For example, the memory controller hub 1526 may provide support for DDR SDRAM memory (e.g., DDR, DDR2, DDR3, etc.). In general, the memory 1540 is a type of random-access memory (RAM). It is often referred to as "system memory".

The memory controller hub 1526 further includes a low-voltage differential signaling interface (LVDS) 1532. The LVDS 1532 may be a so-called LVDS Display Interface (LDI) for support of a display device 1592 (e.g., a CRT, a flat panel, a projector, etc.). A block 1538 includes some examples of technologies that may be supported via the LVDS interface 1532 (e.g., serial digital video, HDMI/DVI, display port). The memory controller hub 1526 also includes one or more PCI-express interfaces (PCI-E) 1534, for example, for support of discrete graphics 1536. Discrete graphics using a PCI-E interface has become an alternative approach to an accelerated graphics port (AGP). For example, the memory controller hub 1526 may include a 16-lane (x16) PCI-E port for an external PCI-E-based graphics card. A system may include AGP or PCI-E for support of graphics. As described herein, a display may be a sensor display (e.g., configured for receipt of input using a stylus, a finger, etc.). As described herein, a sensor display may rely on resistive sensing, optical sensing, or other type of sensing.

The I/O hub controller 1550 includes a variety of interfaces. The example of FIG. 15 includes a SATA interface 1551, one or more PCI-E interfaces 1552 (optionally one or more legacy PCI interfaces), one or more USB interfaces 1553, a LAN interface 1554 (more generally a network interface), a general purpose I/O interface (GPIO) 1555, a low-pin count (LPC) interface 1570, a power management interface 1561, a clock generator interface 1562, an audio interface 1563 (e.g., for speakers 1594), a total cost of operation (TCO) interface 1564, a system management bus interface (e.g., a multi-master serial computer bus interface) 1565, and a serial peripheral flash memory/controller interface (SPI Flash) 1566, which, in the example of FIG. 15, includes BIOS 1568 and boot code 1590. With respect to network connections, the I/O hub controller 1550 may include integrated gigabit Ethernet controller lines multiplexed with a PCI-E interface port. Other network features may operate independent of a PCI-E interface.

The interfaces of the I/O hub controller 1550 provide for communication with various devices, networks, etc. For example, the SATA interface 1551 provides for reading, writing or reading and writing information on one or more drives 1580 such as HDDs, SDDs or a combination thereof. The I/O hub controller 1550 may also include an advanced host controller interface (AHCI) to support one or more drives 1580. The PCI-E interface 1552 allows for wireless connections 1582 to devices, networks, etc. The USB interface 1553 provides for input devices 1584 such as keyboards (KB), one or more optical sensors, mice and various other devices (e.g., microphones, cameras, phones, storage, media players, etc.). On or more other types of sensors may optionally rely on the USB interface 1553 or another interface (e.g., I2C, etc.). As to microphones, the system 1500 of FIG. 15 may include hardware (e.g., audio card) appropriately configured for receipt of sound (e.g., user voice, ambient sound, etc.).

In the example of FIG. 15, the LPC interface 1570 provides for use of one or more ASICs 1571, a trusted platform module (TPM) 1572, a super I/O 1573, a firmware hub 1574, BIOS support 1575 as well as various types of memory 1576 such as ROM 1577, Flash 1578, and non-volatile RAM (NVRAM) 1579. With respect to the TPM 1572, this module may be in the form of a chip that can be used to authenticate software and hardware devices. For example, a TPM may be capable of performing platform authentication and may be used to verify that a system seeking access is the expected system.

The system 1500, upon power on, may be configured to execute boot code 1590 for the BIOS 1568, as stored within the SPI Flash 1566, and thereafter processes data under the control of one or more operating systems and application software (e.g., stored in system memory 1540). An operating system may be stored in any of a variety of locations and accessed, for example, according to instructions of the BIOS 1568. Again, as described herein, a satellite, a base, a server or other machine may include fewer or more features than shown in the system 1500 of FIG. 15. Further, the system 1500 of FIG. 15 is shown as optionally include cell phone circuitry 1595, which may include GSM, CDMA, etc., types of circuitry configured for coordinated operation with one or more of the other features of the system 1500. Also shown in FIG. 15 is battery circuitry 1597, which may provide one or more battery, power, etc., associated features (e.g., optionally to instruct one or more other components of the system 1500). As an example, a SMBus may be operable via a LPC (see, e.g., the LPC interface 1570), via an I2C interface (see, e.g., the SM/I2C interface 1565), etc.

Although examples of methods, devices, systems, etc., have been described in language specific to structural features and/or methodological acts, it is to be understood that the subject matter defined in the appended claims is not necessarily limited to the specific features or acts described. Rather, the specific features and acts are disclosed as examples of forms of implementing the claimed methods, devices, systems, etc.

What is claimed is:

1. A computing device comprising:
a processor;
memory accessible to the processor;
a display operatively coupled to the processor; and
an external shell assembly that comprises an external shell and an array of electronic components, wherein the array of electronic components comprises transducers that comprise different types of electronic components, wherein the different types of electronic components comprise electricity to light transducers that emit light waves and electricity to mechanical motion transducers that emit pressure waves, and wherein the external shell comprises microperforations for passage of the light waves and for passage of the pressure waves.

2. The computing device of claim 1, wherein each of at least some of the transducers comprises a membrane.

3. The computing device of claim 2, wherein the membrane is a strain gauge membrane.

4. The computing device of claim 2, wherein the membrane is a speaker membrane.

5. The computing device of claim 1, wherein each of at least some of the transducers comprises a light emitting diode.

6. The computing device of claim 1, wherein each of at least some of the transducers comprises an ultraviolet radiation emitting diode for sterilization of the external shell via passage of ultraviolet light through at least some of the microperforations.

7. The computing device of claim 1, wherein the array of electronic components comprises one or more batteries.

8. The computing device of claim 7, wherein at least one of the one or more batteries is non-rechargeable.

9. The computing device of claim 7, wherein at least one of the one or more batteries is rechargeable.

10. The computing device of claim 1, wherein the electricity to mechanical motion transducers are operable as mechanical motion to electricity transducers.

11. The computing device of claim 1, wherein the different types of electronic components comprise mechanical motion to electricity transducers.

12. The computing device of claim 1, wherein the external shell assembly forms part of a display housing for the display, and further comprising a keyboard housing for a keyboard, and a hinge assembly that operatively couples the display housing and the keyboard housing, wherein the external shell assembly comprises a display side and a back side, and wherein the external shell of the external shell assembly forms the back side.

13. The computing device of claim 1, comprising a battery and power circuitry operatively coupled to the battery, the processor and the array of electronic components, wherein the power circuitry selectively supplies power to the array of electronic components without supplying power to the processor.

14. The computing device of claim 1, comprising a battery and power circuitry operatively coupled to the battery, the processor and the array of electronic components, wherein the power circuitry selectively supplies power to the array of electronic components while supplying power to the processor.

15. The computing device of claim 1, wherein the array of electronic components is operable independent of operation of the processor.

16. The computing device of claim 1, wherein the array of electronic components is operatively coupled to the processor.

17. The computing device of claim 1, comprising power circuitry that selectively supplies power to the array of electronic components responsive to a power mode of the processor.

18. The computing device of claim 1, wherein each of the microperforations comprises a maximum dimension less than approximately 2 mm.

19. The computing device of claim 1, wherein the different types of electronic components comprise mechanical motion to electricity transducers for touch input, and wherein the microperforations increase resiliency of the external shell for elastic deformation of the external shell responsive to touch force.

20. A computing device comprising:

a processor;

memory accessible to the processor;

a display operatively coupled to the processor; and an external shell assembly that comprises an external shell and an array of electronic components, wherein the array of electronic components comprises transducers, wherein each of at least some of the transducers comprise an ultraviolet radiation emitting diode, and wherein the external shell comprises microperforations for passage of ultraviolet radiation for sterilization of the external shell.

* * * * *